(12) United States Patent
Bakis et al.

(10) Patent No.: US 10,695,176 B2
(45) Date of Patent: *Jun. 30, 2020

(54) PROSTHETIC HEART VALVE DELIVERY APPARATUS

(71) Applicant: Edwards Lifesciences Corporation, Irvine, CA (US)

(72) Inventors: George Bakis, La Habra Heights, CA (US); Thanh V. Nguyen, Irvine, CA (US); Ly Th Phan, Irvine, CA (US); Asher L. Metchik, Hawthorne, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 15/868,741

(22) Filed: Jan. 11, 2018

(65) Prior Publication Data

US 2018/0125656 A1 May 10, 2018

Related U.S. Application Data

(63) Continuation of application No. 14/283,056, filed on May 20, 2014, now Pat. No. 9,867,700.

(60) Provisional application No. 61/825,476, filed on May 20, 2013.

(51) Int. Cl.
*A61F 2/24* (2006.01)

(52) U.S. Cl.
CPC .......... *A61F 2/2436* (2013.01); *A61F 2/2418* (2013.01); *A61F 2/2439* (2013.01)

(58) Field of Classification Search
CPC ..... A61F 2/2436; A61F 2/2418; A61F 2/2439
See application file for complete search history.

(56) References Cited

U.S. PATENT DOCUMENTS

| | | |
|---|---|---|
| 4,035,849 A | 7/1977 | Angell et al. |
| 4,592,340 A | 6/1986 | Boyles |
| 4,994,077 A | 2/1991 | Dobben |
| 5,059,177 A | 10/1991 | Towne et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,639,274 A | 6/1997 | Fischell et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Katherine M Rodjom
(74) *Attorney, Agent, or Firm* — Klarquist Sparkman, LLP; Hans P. Smith

(57) ABSTRACT

Certain embodiments of the present disclosure provide a prosthetic valve (e.g., prosthetic heart valve) and a valve delivery apparatus for delivery of the prosthetic valve to a native valve site via the human vasculature. The delivery apparatus is particularly suited for advancing a prosthetic heart valve through the aorta (i.e., in a retrograde approach) for replacing a diseased native aortic valve. The delivery apparatus in particular embodiments is configured to deploy a prosthetic valve from a delivery sheath in a precise and controlled manner at the target location within the body.

15 Claims, 26 Drawing Sheets

(56) References Cited

U.S. PATENT DOCUMENTS

| | | |
|---|---|---|
| 5,728,068 A | 3/1998 | Leone et al. |
| 5,840,081 A | 11/1998 | Andersen et al. |
| 5,968,068 A | 10/1999 | Dehdashtian et al. |
| 6,168,614 B1 | 1/2001 | Andersen et al. |
| 6,217,585 B1 | 4/2001 | Houser et al. |
| 6,379,372 B1 | 4/2002 | Dehdashtian et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,749,266 B2 | 7/2010 | Forster et al. |
| 7,785,366 B2 | 8/2010 | Maurer et al. |
| 7,959,661 B2 | 6/2011 | Hijikema et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,449,606 B2 | 5/2013 | Eliasen et al. |
| 8,652,145 B2 | 2/2014 | Maimon et al. |
| 8,652,202 B2 | 2/2014 | Alon et al. |
| 9,155,619 B2 | 10/2015 | Liu et al. |
| 9,168,131 B2 | 10/2015 | Yohanan et al. |
| 2002/0032481 A1 | 3/2002 | Gabbay |
| 2003/0040792 A1 | 2/2003 | Gabbay |
| 2003/0050694 A1 | 3/2003 | Yang et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0236411 A1 | 11/2004 | Sarao et al. |
| 2004/0260389 A1 | 12/2004 | Case et al. |
| 2005/0075731 A1 | 4/2005 | Artof et al. |
| 2005/0080474 A1 | 4/2005 | Andreas et al. |
| 2005/0096736 A1 | 5/2005 | Osse et al. |
| 2005/0113910 A1 | 5/2005 | Paniagua et al. |
| 2005/0137688 A1 | 6/2005 | Salahieh et al. |
| 2005/0137693 A1 | 6/2005 | Haug et al. |
| 2005/0137697 A1 | 6/2005 | Salahieh et al. |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2006/0149360 A1 | 7/2006 | Schwammenthal et al. |
| 2006/0259136 A1 | 11/2006 | Nguyen et al. |
| 2006/0276813 A1 | 12/2006 | Greenberg |
| 2006/0287719 A1 | 12/2006 | Rowe et al. |
| 2007/0005131 A1 | 1/2007 | Taylor |
| 2007/0073389 A1 | 3/2007 | Bolduc et al. |
| 2007/0203575 A1 | 8/2007 | Forster et al. |
| 2007/0213813 A1 | 9/2007 | Von Segesser et al. |
| 2007/0265700 A1 | 11/2007 | Eliasen et al. |
| 2008/0125853 A1 | 5/2008 | Bailey et al. |
| 2008/0161911 A1 | 7/2008 | Revuelta et al. |
| 2008/0294230 A1 | 11/2008 | Parker |
| 2008/0319526 A1 | 12/2008 | Hill et al. |
| 2009/0157175 A1 | 6/2009 | Benichou |
| 2009/0204202 A1 | 8/2009 | Dierking et al. |
| 2009/0276040 A1 | 11/2009 | Rowe et al. |
| 2009/0281619 A1* | 11/2009 | Le .................. A61F 2/2433 623/2.11 |
| 2009/0319037 A1 | 12/2009 | Rowe et al. |
| 2010/0049313 A1* | 2/2010 | Alon .................. A61F 2/2418 623/2.11 |
| 2010/0191326 A1 | 7/2010 | Alkhatib |
| 2010/0198347 A1 | 8/2010 | Zakay et al. |
| 2011/0015729 A1 | 1/2011 | Jimenez et al. |
| 2011/0040374 A1 | 2/2011 | Goetz et al. |
| 2012/0071969 A1 | 3/2012 | Li et al. |
| 2012/0123529 A1 | 5/2012 | Levi et al. |
| 2012/0245676 A1 | 9/2012 | Dierking et al. |
| 2013/0296999 A1 | 11/2013 | Burriesci et al. |
| 2013/0317598 A1 | 11/2013 | Rowe et al. |
| 2014/0343670 A1 | 11/2014 | Bakis et al. |
| 2015/0157455 A1 | 6/2015 | Hoang et al. |
| 2017/0056149 A1 | 3/2017 | Rajpara et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |

FOREIGN PATENT DOCUMENTS

| | | |
|---|---|---|
| EP | 0592410 A1 | 4/1994 |
| EP | 0850607 A1 | 7/1998 |
| EP | 1796597 A2 | 6/2007 |
| FR | 2815844 A1 | 5/2002 |
| JP | 2009511229 A | 3/2009 |
| JP | 2010531709 A | 9/2010 |
| JP | 2011509806 A | 3/2011 |
| JP | 2011510788 A | 4/2011 |
| JP | 2014513585 A | 6/2014 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 05/102015 | 11/2005 |
| WO | 06/111391 | 10/2006 |
| WO | 06/138173 | 12/2006 |
| WO | 2007047488 A2 | 4/2007 |
| WO | 2007067942 A1 | 6/2007 |
| WO | 2008125153 A1 | 10/2008 |
| WO | 2010121076 A2 | 10/2010 |
| WO | 2012116368 A2 | 8/2012 |

* cited by examiner

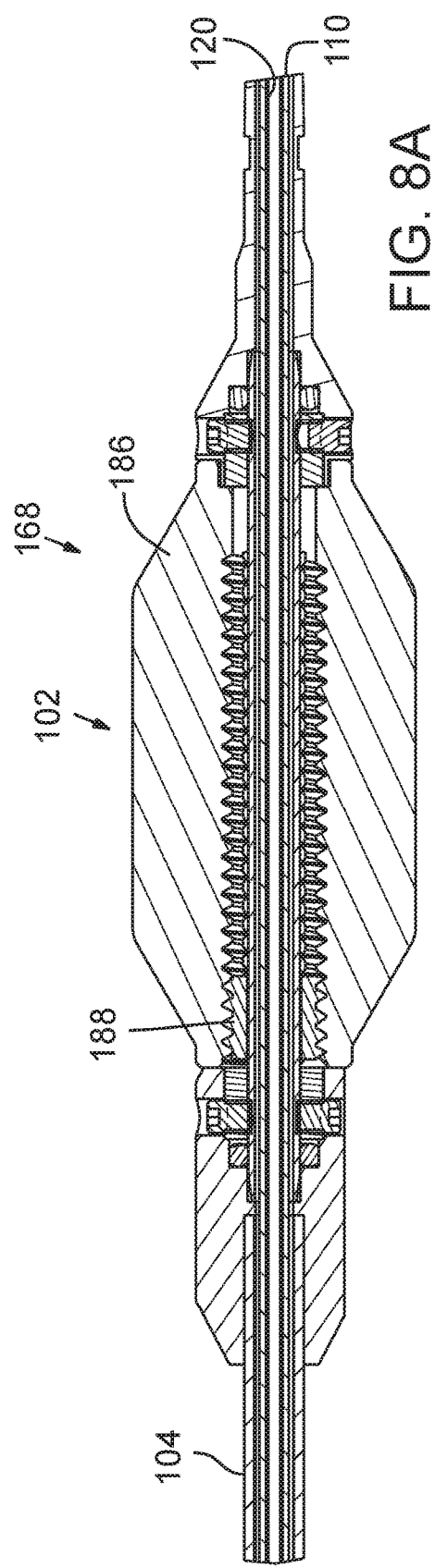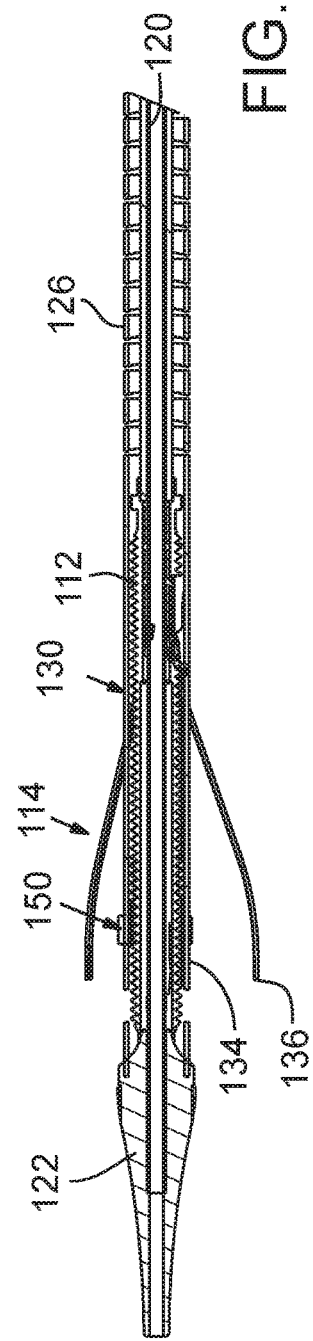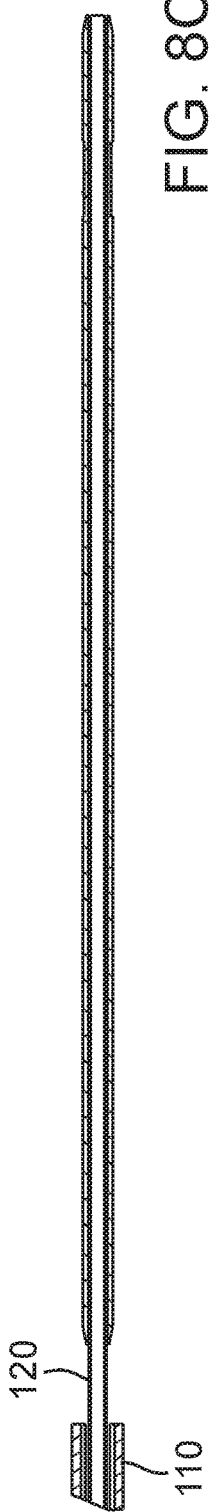

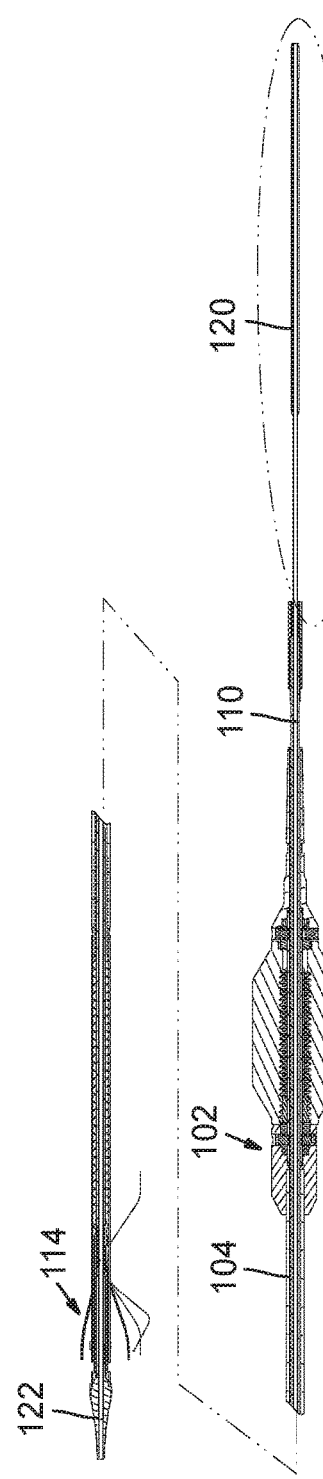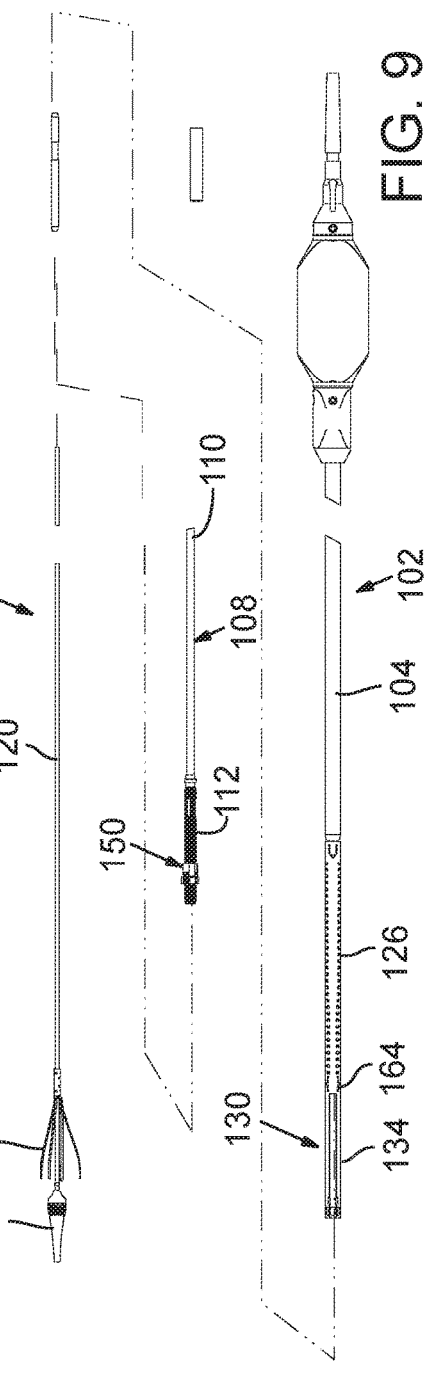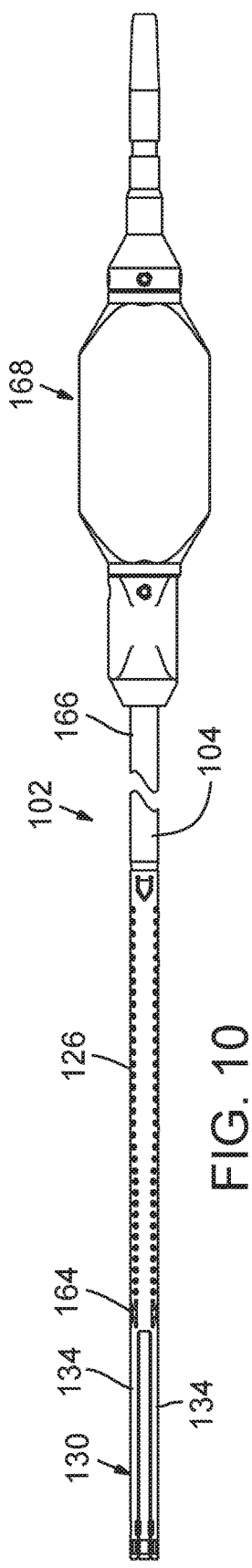

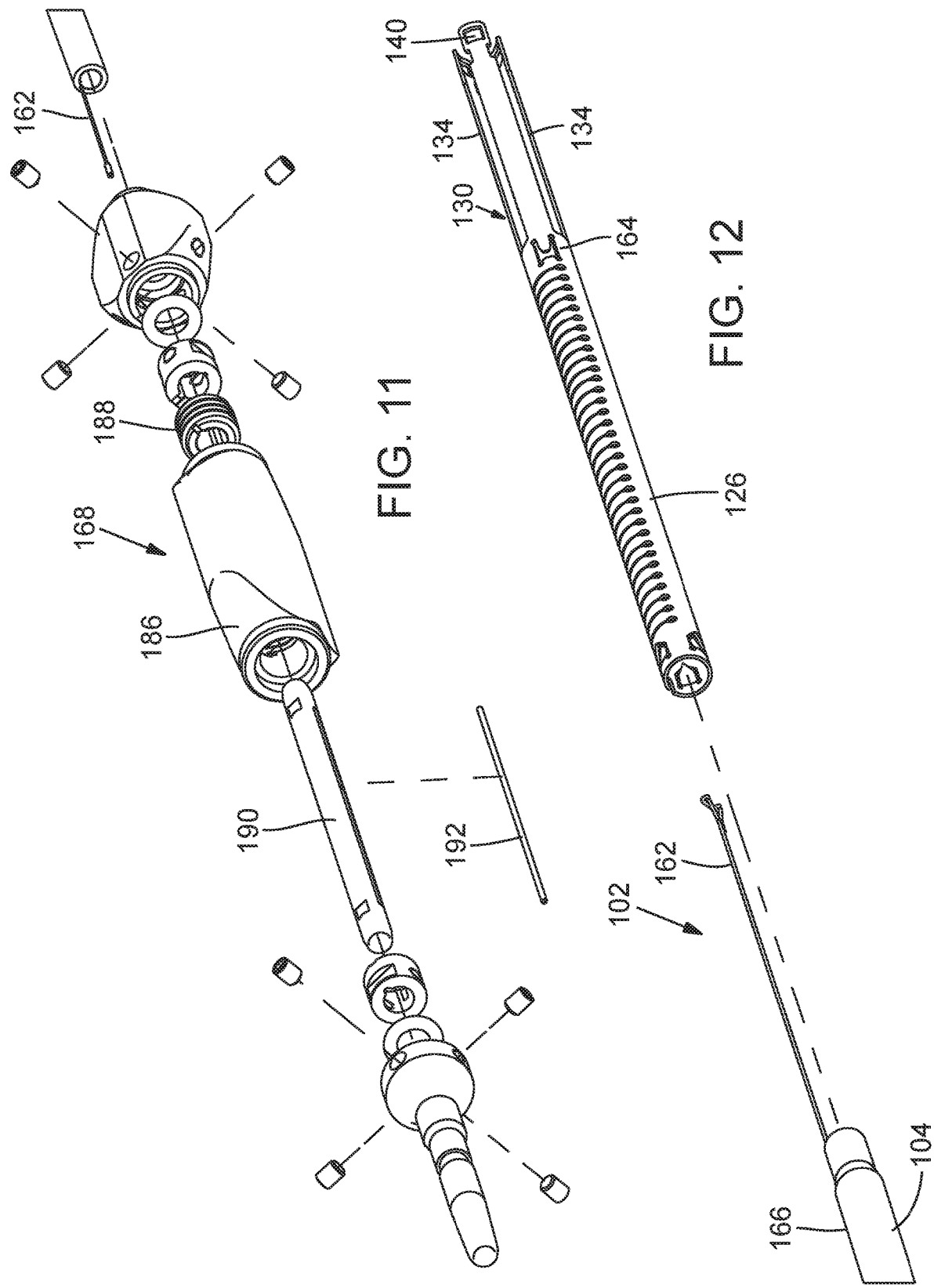

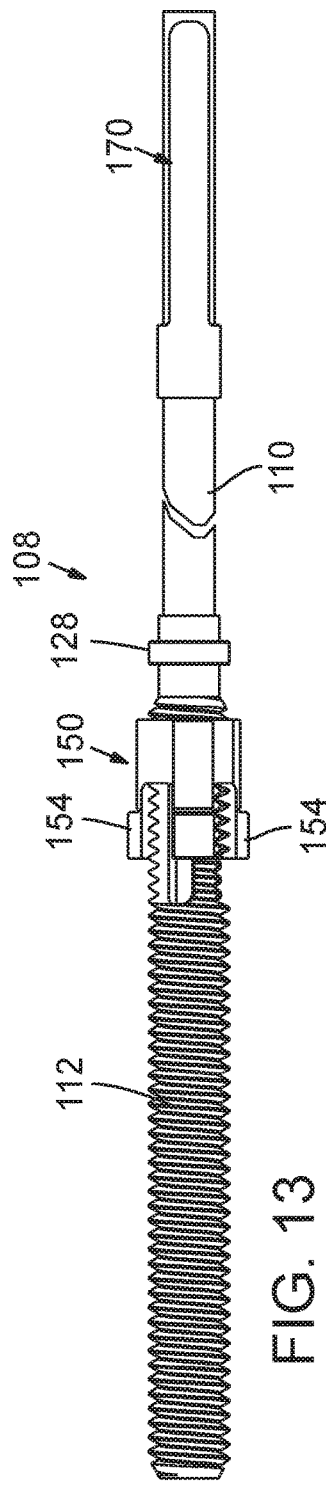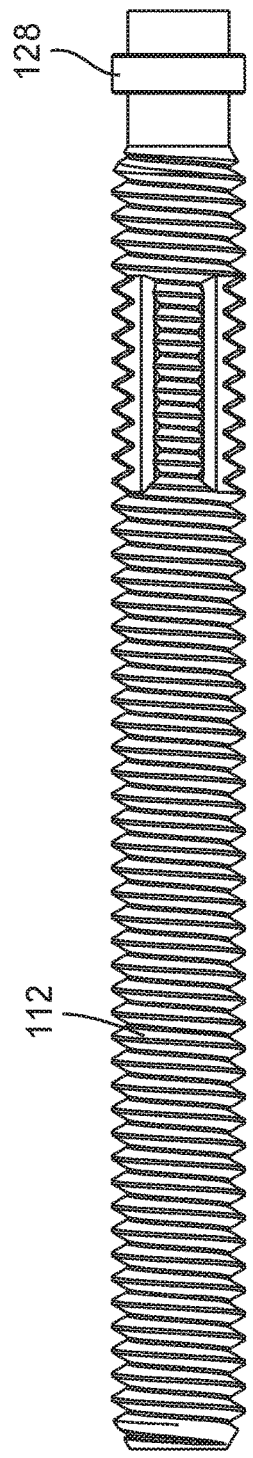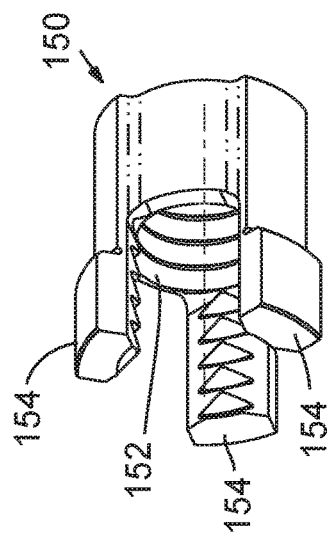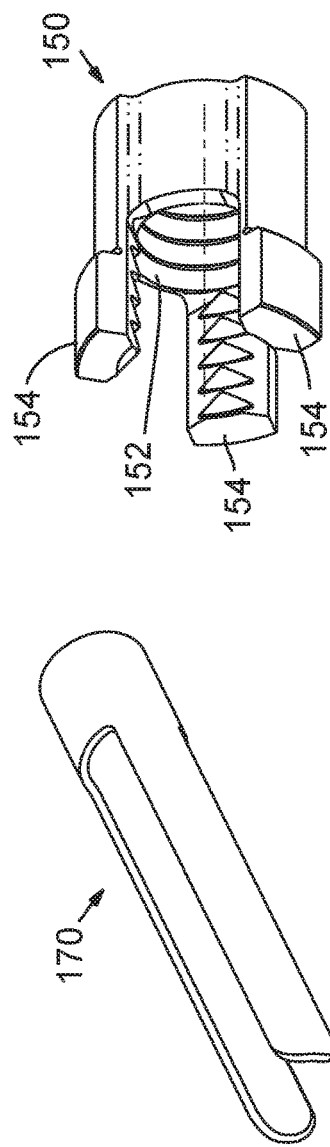

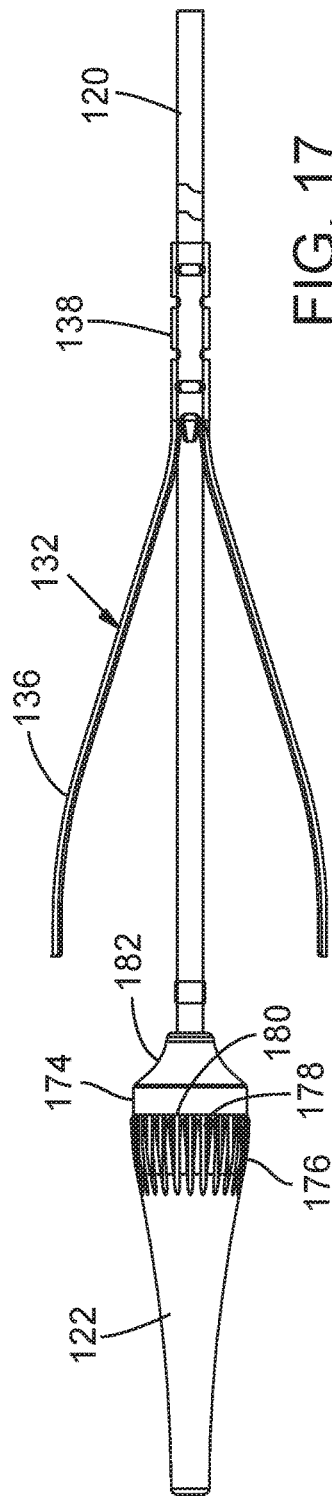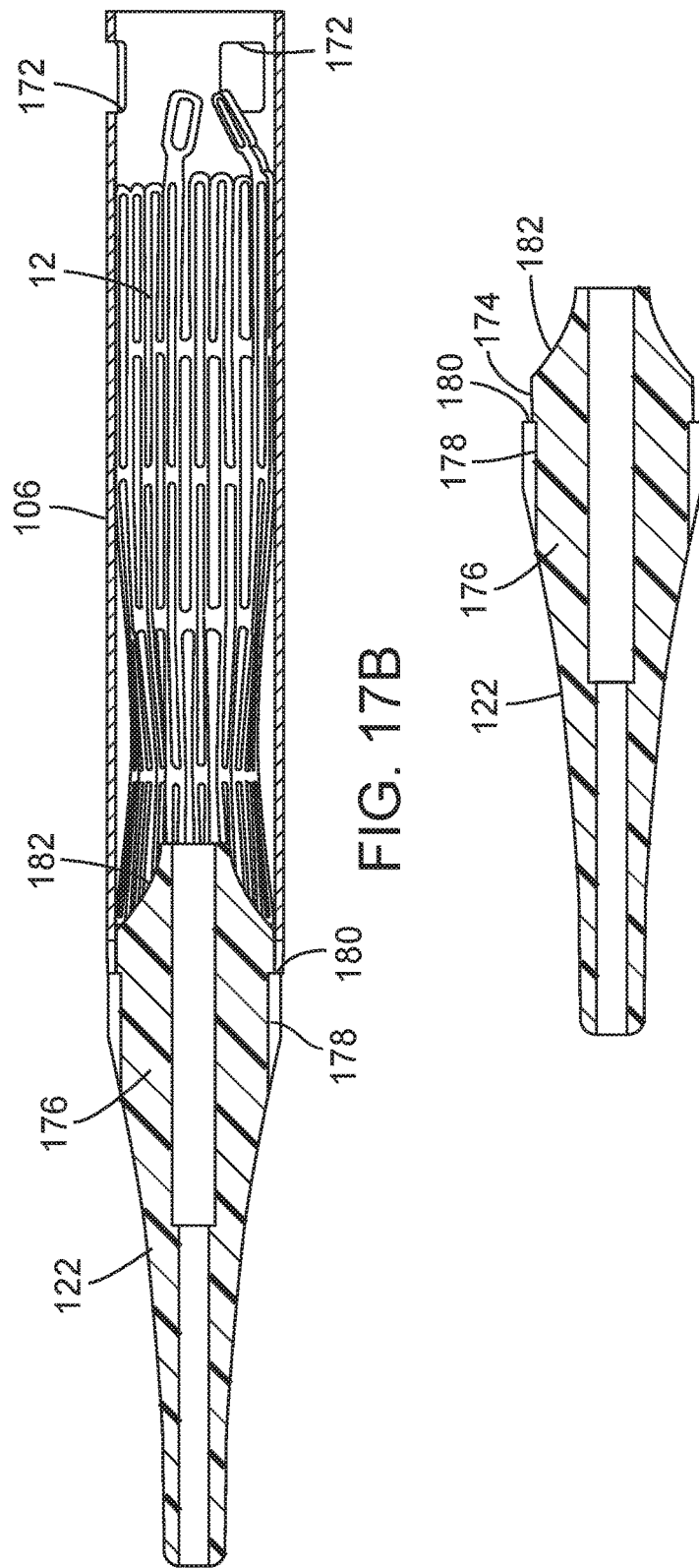

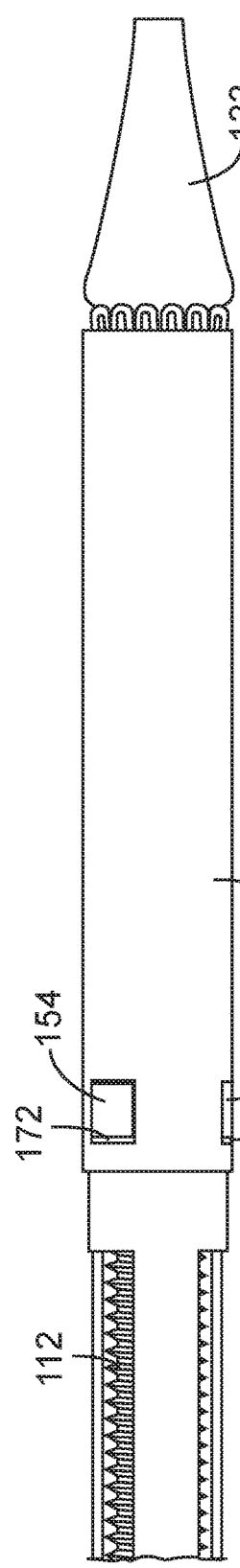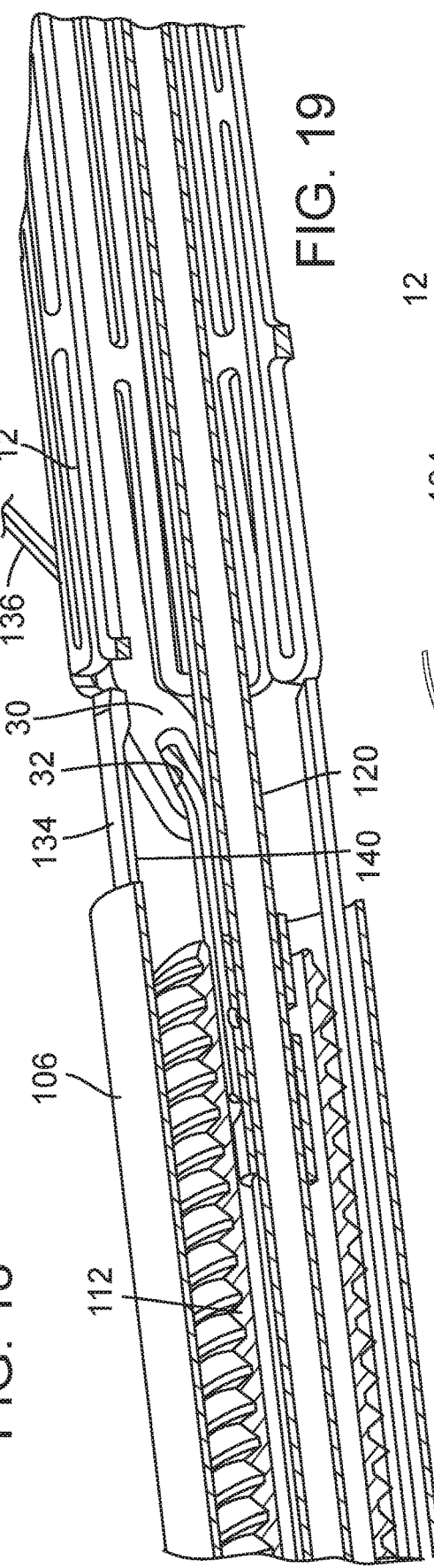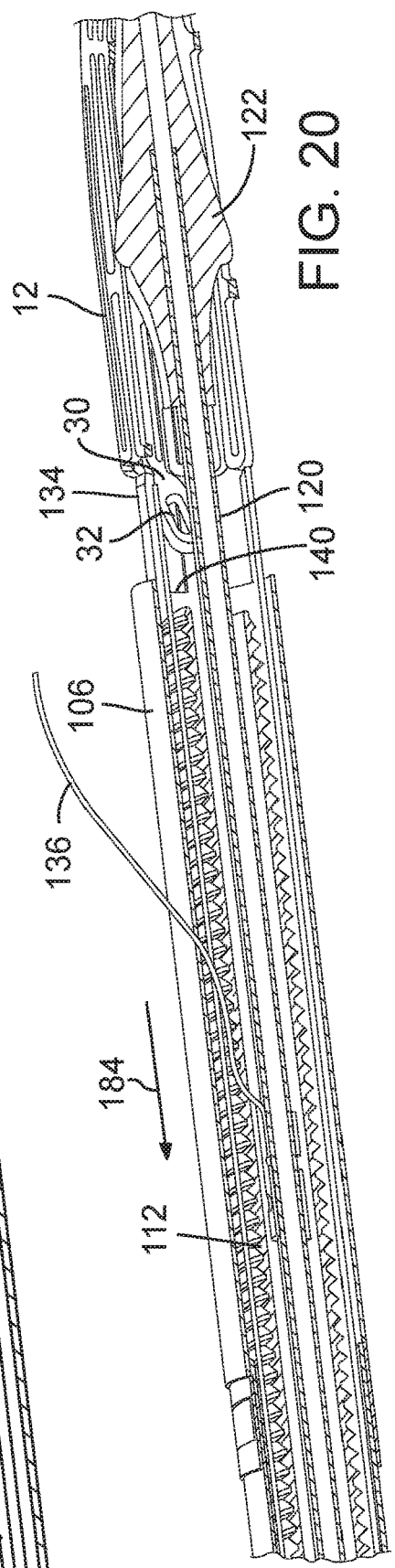

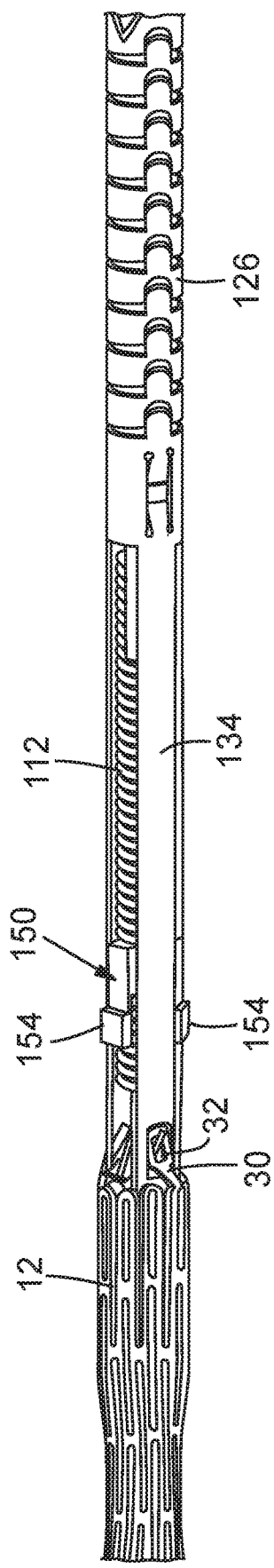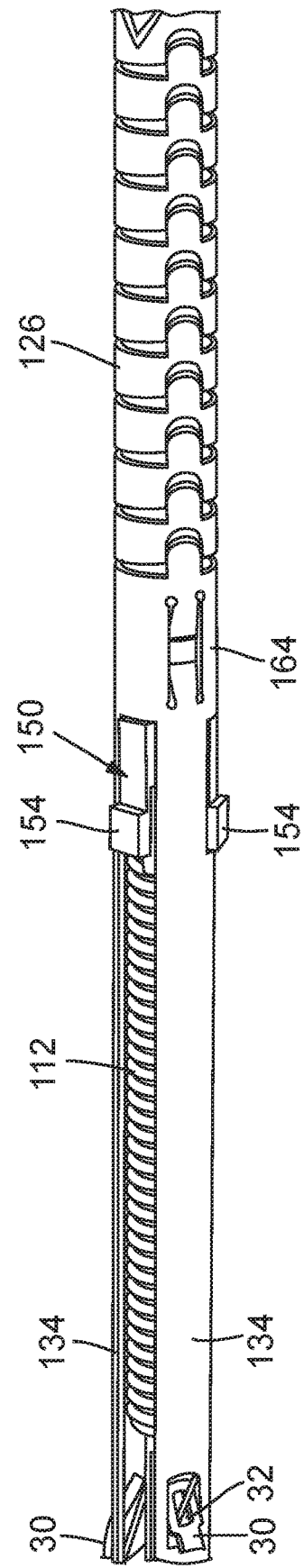

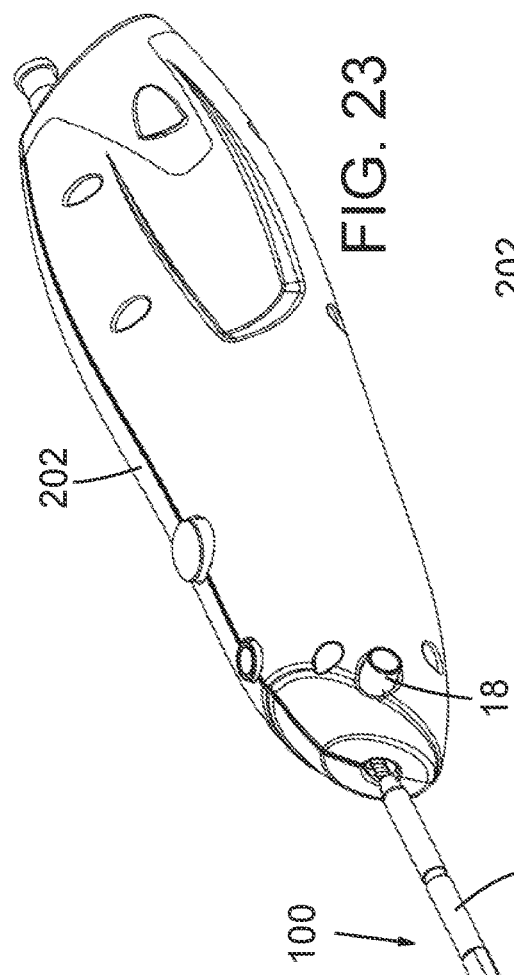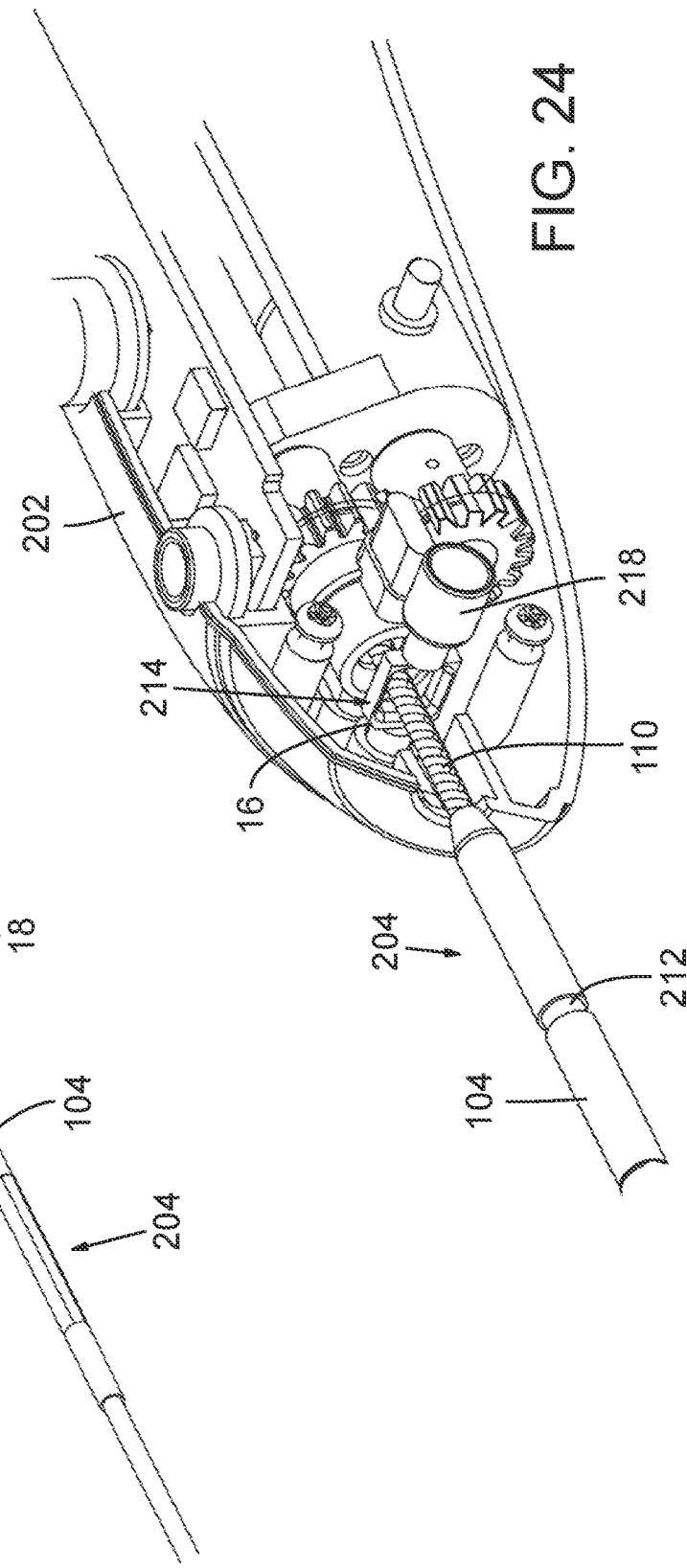

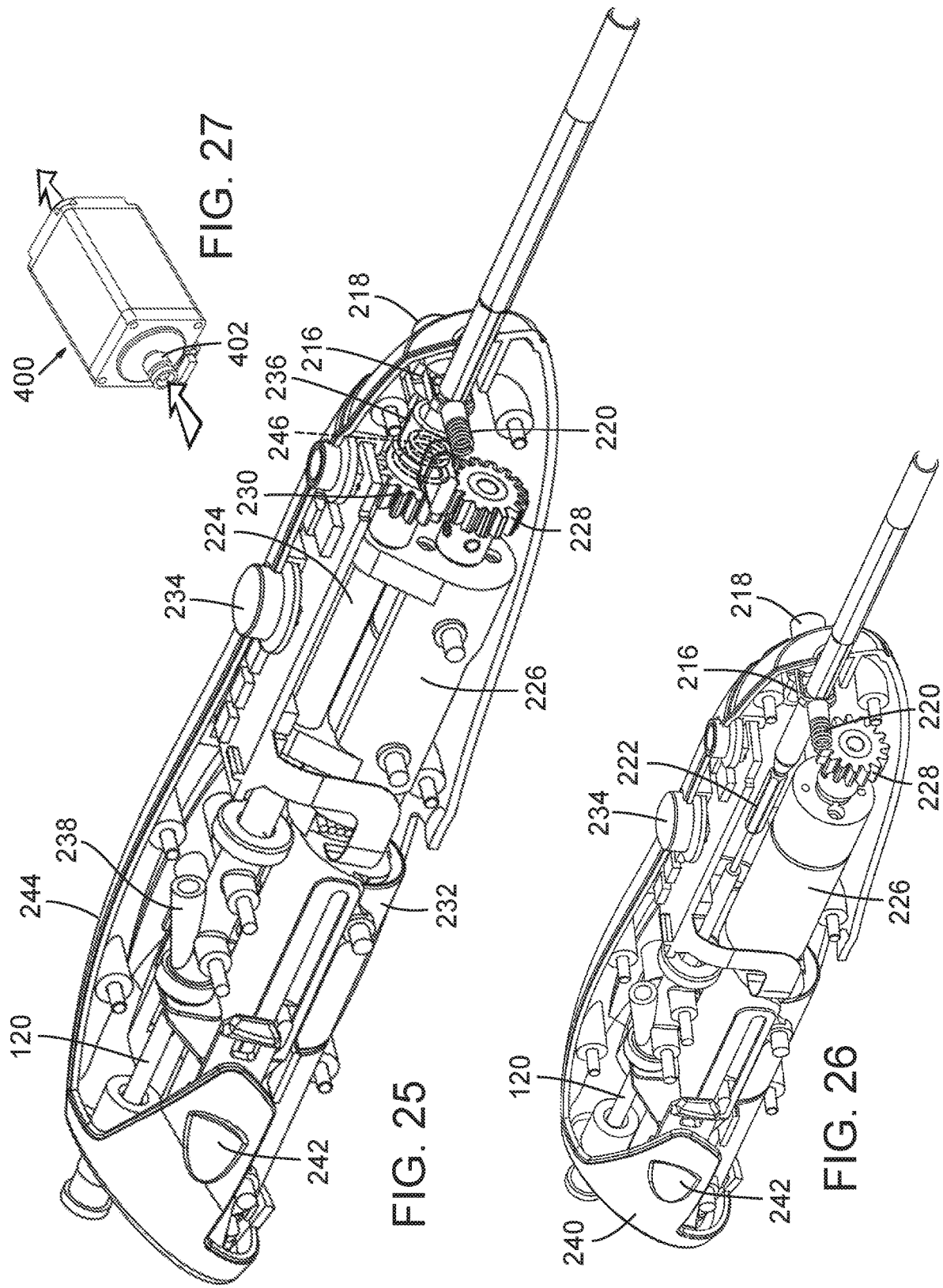

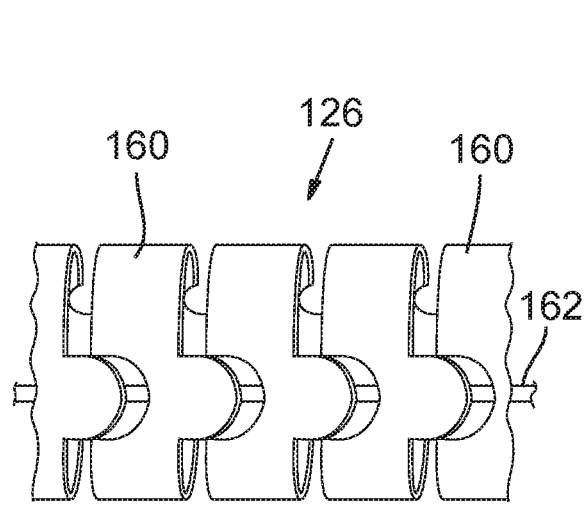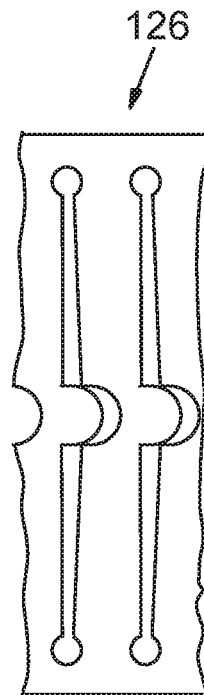
FIG. 28A
FIG. 28B
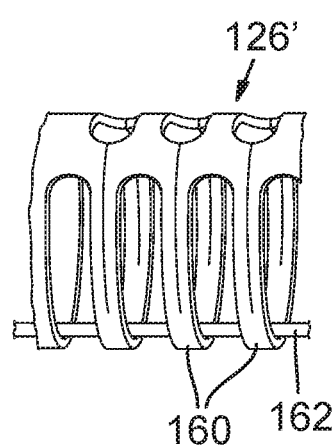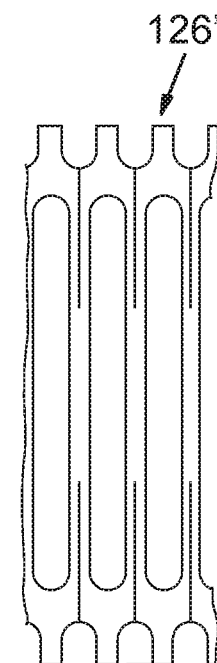
FIG. 29A
FIG. 29B

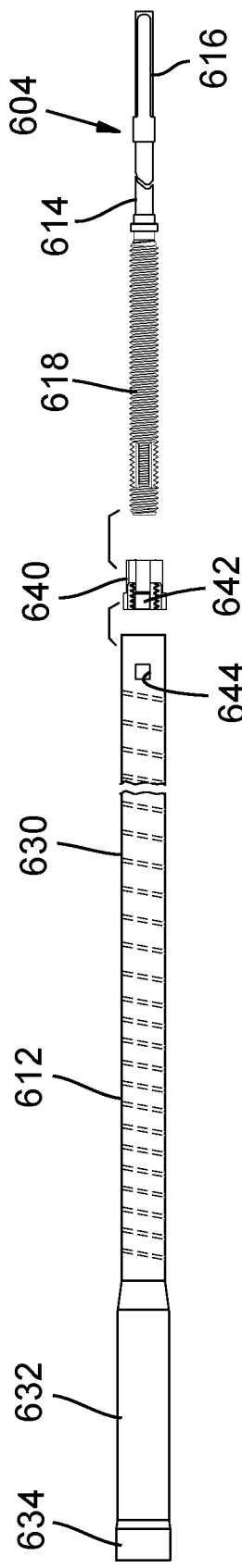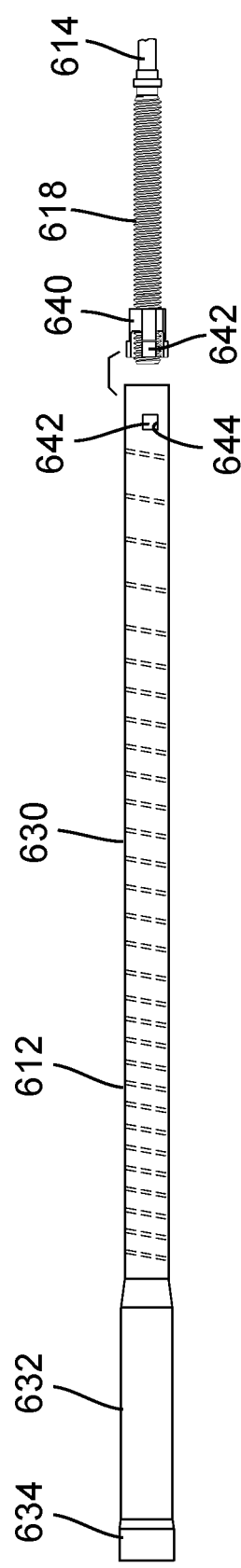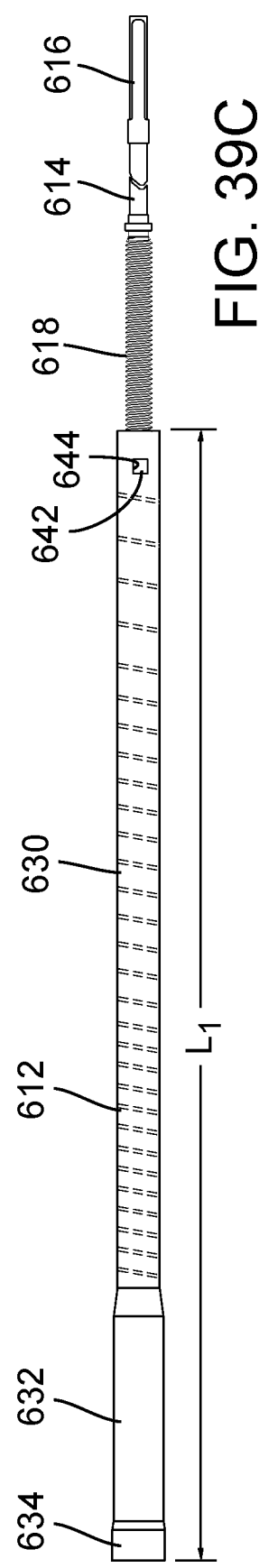

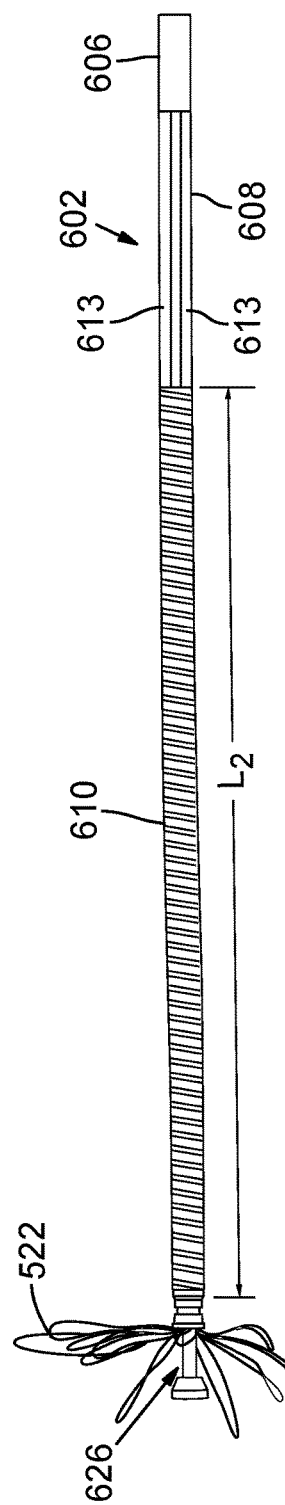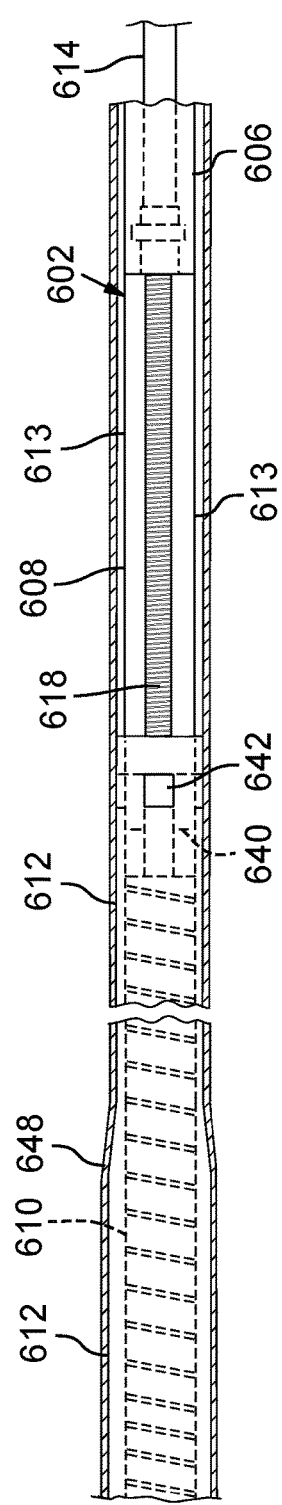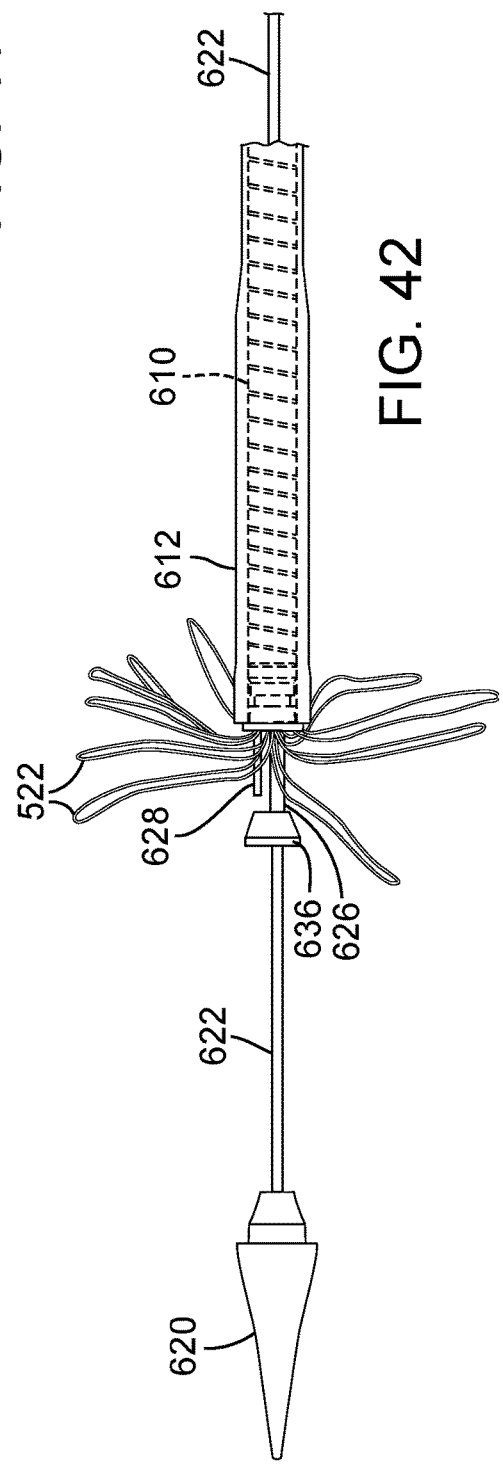

PROSTHETIC HEART VALVE DELIVERY APPARATUS

CROSS-REFERENCE TO RELATED APPLICATION

This application is a continuation of U.S. patent application Ser. No. 14/283,056, field May 20, 2014, now U.S. Pat. No. 9,867,700, which claims priority to U.S. Provisional Patent Application No. 61/825,476, filed May 20, 2013, the disclosures all of which are incorporated by reference in their entireties.

FIELD

The present invention concerns embodiments of a prosthetic valve (e.g., prosthetic heart valve) and a delivery apparatus for implanting a prosthetic valve.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

Balloon-expandable prosthetic valves typically are preferred for replacing calcified native valves because the catheter balloon can apply sufficient expanding force to anchor the frame of the prosthetic valve to the surrounding calcified tissue. On the other hand, self-expanding prosthetic valves sometimes are preferred for replacing a defective, non-stenotic (non-calcified) native valve, although they also can be used to replace stenotic valves. One drawback associated with implanting a self-expanding prosthetic valve is that as the operator begins to advance the prosthetic valve from the open end of the delivery sheath, the prosthetic valve tends to "jump" out very quickly from the end of the sheath; in other words, the outward biasing force of the prosthetic valve's frame tends to cause the prosthetic valve to be ejected very quickly from the distal end of the delivery sheath, making it difficult to deliver the prosthetic valve from the sheath in a precise and controlled manner and increasing the risk of trauma to the patient.

Another problem associated with implanting a percutaneous prosthetic valve in a non-stenotic native valve is that the prosthetic valve may not be able to exert sufficient force against the surrounding tissue to resist migration of the prosthetic valve. Typically, the stent of the prosthetic valve must be provided with additional anchoring or attachment devices to assist in anchoring the prosthetic valve to the surrounding tissue. Moreover, such anchoring devices or portions of the stent that assist in anchoring the prosthetic valve typically extend into and become fixed to non-diseased areas of the vasculature, which can result in complications if future intervention is required, for example, if the prosthetic valve needs to be removed from the patient.

SUMMARY

Certain embodiments of the present disclosure provide a prosthetic valve (e.g., a prosthetic heart valve) and a valve delivery apparatus for delivery of the prosthetic valve to a native valve site via the human vasculature. The delivery apparatus is particularly suited for advancing a prosthetic valve through the aorta (i.e., in a retrograde approach) for replacing a diseased native aortic valve. The delivery apparatus in particular embodiments is configured to deploy a prosthetic valve from a delivery sheath in a precise and controlled manner at the target location within the body.

In an aspect, a delivery assembly comprises a prosthetic valve, an elongate shaft located proximal to the prosthetic valve, a suture-retention member located distal to the shaft, a slidable release member, and an outer sheath. The prosthetic valve can comprise a self-expandable stent having a plurality of apices spaced circumferentially around a first end portion of the stent, wherein each apex has an aperture. The suture-retention member can comprise a proximal portion and a distal portion spaced from the proximal portion, the proximal portion being coupled to the shaft. The at least one slidable release member can extend through the proximal portion and the distal portion of the suture-retention member and a plurality of suture loops extending from the proximal portion of the suture-retention member. The plurality of suture loops can extend through the apertures in the apices of the stent and around the release member at a location between the proximal and distal portions of suture-retention member, such that at least one of the suture loops extends through the aperture of every apex. The outer sheath can be advanced over the prosthetic valve to retain the prosthetic valve in a radially compressed state, and can be retracted relative to the prosthetic valve to permit radial expansion of the prosthetic valve while the stent remains connected to the suture-retention member via the suture loops. After the entirety of the prosthetic valve is deployed from the sheath, the sheath can be advanced distally back over the prosthetic valve to cause the prosthetic valve to radially collapse as it is recaptured by the sheath.

In some embodiments, the suture loops are formed from a single length of suture material.

In some embodiments, the shaft comprises a first shaft and the assembly further comprises a second shaft extending at least partially through the first shaft, wherein the outer sheath can be advanced or retracted relative to the prosthetic valve by rotating the second shaft relative to the first shaft.

In some embodiments, the at least one release member is slidable relative to the suture-retention member, and when the release member is retracted proximally such that a distal end of the release member is proximal to the distal portion of the suture-retention member, the suture loops can slide off the distal end of the release member, thereby releasing the prosthetic valve from the suture-retention member.

In some embodiments, at least a portion of the outer sheath comprises a slotted metal tube.

In some embodiments, a distal end portion of the outer sheath comprises a delivery capsule connected to a distal end of the slotted metal tube, the delivery capsule configured to extend over and retain the prosthetic valve in the radially compressed state.

In some embodiments, the delivery capsule comprises a polymer sleeve.

In some embodiments, the sheath is at least about 3-10 cm is length and no greater than about 40 cm in length.

In some embodiments, at least one of the suture loops has a greater thickness than others of the suture loops.

In another aspect, a delivery apparatus for implanting a prosthetic valve comprises a first elongated shaft having a proximal end portion and a distal end portion, a second elongated shaft extending through the first shaft and having a proximal end portion and a distal end portion, and a delivery sheath having a distal end portion configured to receive and retain a prosthetic valve in a compressed delivery state and a proximal end portion connected to the distal end portion of the second elongated shaft. The second shaft can be rotatable relative to the first shaft but fixed against axial movement relative to the first shaft. The proximal end portion of the delivery sheath can be more flexible than the distal end portion of the sheath. The delivery sheath can be, without limitation, at least about 3-5 cm in length and no greater than about 40 cm in length. The second shaft can be configured to be rotatable relative to the first shaft such that rotation of the second shaft causes the delivery sheath to move axially relative to the first and second shafts.

In some embodiments, the delivery apparatus further comprises a screw connected to a distal end of the second shaft, and a nut mounted on the screw and connected to the delivery sheath such that rotation of the second shaft and the screw causes axial movement of the nut relative to the screw, thereby producing axial movement of the delivery sheath.

In some embodiments, the proximal end portion of the delivery sheath is between about 5 cm and about 30 cm in length.

In some embodiments, the distal end portion of the first shaft extends through the delivery sheath and comprises a slotted metal tube.

In some embodiments, the delivery apparatus further comprises a suture-retention member connected to the distal end portion of the first shaft, a plurality of suture loops extending from the suture-retention member and configured to extend through openings in a frame of the prosthetic valve, and at least one slidable release member configured to extend through the suture-retention member and the suture loops to releasably secure the prosthetic valve to the suture-retention member.

In some embodiments, the suture-retention member comprises a proximal portion and a distal portion spaced axially apart from the first portion and the release member is slidable relative to the suture-retention member, between a first position extending through the proximal and distal portions of the suture-retention member and a second position in which the release member is retracted to a location proximal of the distal portion of the suture-retention member. When the release member is in the first position and the suture loops extend through the openings of the frame and around the release member at a location between the proximal and distal portions, the prosthetic valve is secured to the suture-retention member. When the release member is in the second position, the suture loops can slide off a distal end of the release member to release the prosthetic valve from the suture-retention member.

In some embodiments, the at least one release member comprises a plurality of release members extending through the suture-retention member.

In some embodiments, the proximal portion of the outer sheath comprises a slotted metal tube.

In some embodiments, the distal end portion of the outer sheath comprises a delivery capsule connected to a distal end of the slotted metal tube. The delivery capsule can be configured to extend over and retain the prosthetic valve in the compressed delivery state. In some embodiments, the delivery capsule comprises a polymer sleeve.

In another aspect, a method for delivering a prosthetic valve to the aortic annulus of the heart comprises inserting an elongated delivery apparatus into a femoral artery of a patient, the delivery apparatus comprising a delivery sheath containing the prosthetic valve in a radially compressed state. The method can further comprise advancing the delivery apparatus through the aorta until the prosthetic valve is at an implantation location within the aortic annulus, wherein when the prosthetic valve is at the implantation location, the delivery sheath extends through the ascending aorta and the aortic arch, and a proximal end of the delivery sheath is within the descending aorta. The method can further comprise retracting the delivery sheath relative to the prosthetic valve to deploy the prosthetic valve from a distal end of the delivery sheath.

In some embodiments, the delivery sheath is at least about 3-5 cm and no greater than 40 cm in length.

In some embodiments, the delivery sheath comprises a distal end portion and a proximal end portion that is more flexible than the distal end portion. The distal end portion of the sheath can extend over and retain the prosthetic valve in the radially compressed state during the acts of the inserting and advancing the delivery apparatus, and the proximal end portion can extend through the ascending aorta, the aortic arch and into the descending aorta when the prosthetic valve is at the implantation location.

In some embodiments, the prosthetic valve is releasably secured to the delivery apparatus via a plural of suture loops.

In some embodiments, the act of retracting the delivery sheath comprises deploying the entire prosthetic valve from the delivery sheath and allowing the prosthetic valve to radially expand while still secured to the delivery apparatus via the suture loops.

In some embodiments, the method further comprises, after deploying the entire prosthetic valve from the delivery sheath, recapturing the prosthetic valve by advancing the delivery sheath distally back over the prosthetic valve.

In another aspect, a method for delivering a prosthetic valve to a native valve annulus of the heart comprises inserting an elongated delivery apparatus into the vasculature of a patient, the delivery apparatus comprising a delivery sheath containing the prosthetic valve in a radially compressed state, wherein the prosthetic valve is releasably secured to the delivery apparatus via a plural of suture loops. The method can further comprise retracting the delivery sheath relative to the prosthetic valve to deploy the entire prosthetic valve from the delivery sheath, allowing the prosthetic valve to radially expand while still secured to the delivery apparatus via the suture loops. The method can further comprise, after deploying the entire prosthetic valve from the delivery sheath, recapturing the prosthetic valve by advancing the delivery sheath distally back over the prosthetic valve.

BRIEF DESCRIPTION OF THE DRAWINGS

FIG. 8 is a cross-sectional view of an embodiment of a delivery apparatus that can be used to deliver and implant a prosthetic valve, such as the prosthetic valve shown in FIG. 1. FIGS. 8A-8C are enlarged cross-sectional views of sections of FIG. 8.

FIG. 9 is an exploded view of the delivery apparatus of FIG. 8.

FIG. 10 is a side view of the guide catheter of the delivery apparatus of FIG. 8.

FIG. 11 is a perspective, exploded view of the proximal end portion of the guide catheter of FIG. 10.

FIG. 12 is a perspective, exploded view of the distal end portion of the guide catheter of FIG. 10.

FIG. 13 is a side view of the torque shaft catheter of the delivery apparatus of FIG. 8.

FIG. 14 is an enlarged side view of the rotatable screw of the torque shaft catheter of FIG. 13.

FIG. 15 is an enlarged perspective view of a coupling member disposed at the end of the torque shaft.

FIG. 16 is an enlarged perspective view of the threaded nut used in the torque shaft catheter of FIG. 13.

FIG. 17 is an enlarged side view of the distal end portion of the nose cone catheter of the delivery apparatus of FIG. 8.

FIG. 17A is an enlarged, cross-sectional view of the nose cone of the catheter shown FIG. 17.

FIG. 17B is an enlarged cross-sectional view of the distal end portion of the delivery apparatus of FIG. 8 showing the stent of a prosthetic valve retained in a compressed state within a delivery sheath.

FIG. 18 is an enlarged side view of the distal end portion of the delivery apparatus of FIG. 8 showing the delivery sheath in a delivery position covering a prosthetic valve in a compressed state for delivery into a patient.

FIG. 19 is an enlarged cross-sectional view of a section of the distal end portion of the delivery apparatus of FIG. 8 showing the valve-retaining mechanism securing the stent of a prosthetic valve to the delivery apparatus.

FIG. 20 is an enlarged cross-sectional view similar to FIG. 19, showing the inner fork of the valve-retaining mechanism in a release position for releasing the prosthetic valve from the delivery apparatus.

FIGS. 21 and 22 are enlarged side views of distal end portion of the delivery apparatus of FIG. 8, illustrating the operation of the torque shaft for deploying a prosthetic valve from a delivery sheath.

FIGS. 23-26 are various views of an embodiment of a motorized delivery apparatus that can be used to operate the torque shaft of the delivery apparatus shown in FIG. 8.

FIG. 27 is a perspective view of an alternative motor that can be used to operate the torque shaft of the delivery apparatus shown in FIG. 8.

FIG. 28A is an enlarged view of a distal segment of the guide catheter shaft of FIG. 10.

FIG. 28B shows the cut pattern for forming the portion of the shaft shown in FIG. 28A, such as by laser cutting a metal tube.

FIG. 29A is an enlarged view of a distal segment of a guide catheter shaft, according to another embodiment.

FIG. 29B shows the cut pattern for forming the shaft of FIG. 29A, such as by laser cutting a metal tube.

FIG. 39A is a top view of a delivery cylinder and screw mechanism for use in the delivery assembly of FIG. 38. The screw mechanism can be used to advance and retract the delivery cylinder. The delivery cylinder, screw member and nut are shown separately.

FIG. 39B is a top view of the delivery cylinder and screw mechanism of FIG. 39A, with the nut is mounted on the screw member and the delivery cylinder shown separately.

FIG. 39C is a top view of the delivery cylinder and screw mechanism of FIG. 39A, with a tab portion of the nut (mounted on the screw member) extending through a proximally-located window of the delivery cylinder.

FIG. 40 is a top view of the distal end portion of the first catheter of the delivery apparatus of FIG. 38.

FIG. 41 is a top view of a section of the delivery apparatus of FIG. 38, showing a screw mechanism coupled to a delivery sheath.

FIG. 42 is a top view of the distal end portion of the delivery apparatus of FIG. 38, showing the delivery sheath retracted to a proximal position.

DETAILED DESCRIPTION

Figure 1:
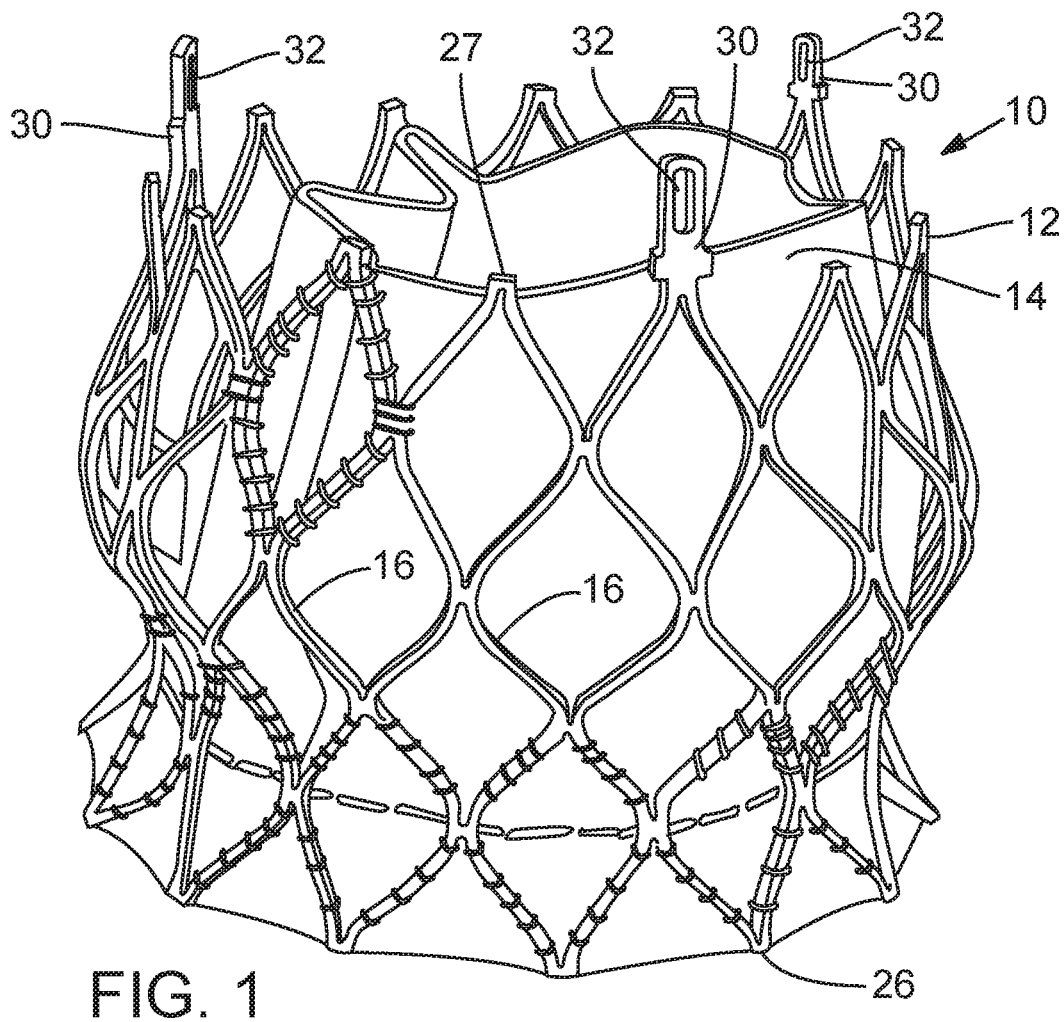
FIG. 1 is a perspective view of a prosthetic valve that can be used to replace the native aortic valve of the heart, according to one embodiment.

Referring first to FIG. 1, there is shown a prosthetic aortic heart valve 10, according to one embodiment. The prosthetic valve 10 includes an expandable frame member, or stent, 12 that supports a flexible leaflet section 14. The prosthetic valve 10 is radially compressible to a compressed state for delivery through the body to a deployment site and expandable to its functional size shown in FIG. 1 at the deployment site. In certain embodiments, the prosthetic valve 10 is self-expanding; that is, the prosthetic valve can radially expand to its functional size when advanced from the distal end of a delivery sheath. Apparatuses particularly suited for percutaneous delivery and implantation of a self-expanding prosthetic valve are described in detail below. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon, as known in the art.

The illustrated prosthetic valve 10 is adapted to be deployed in the native aortic annulus, although it also can be used to replace the other native valves of the heart. Moreover, the prosthetic valve 10 can be adapted to replace other valves within the body, such venous valves.

Figure 3:
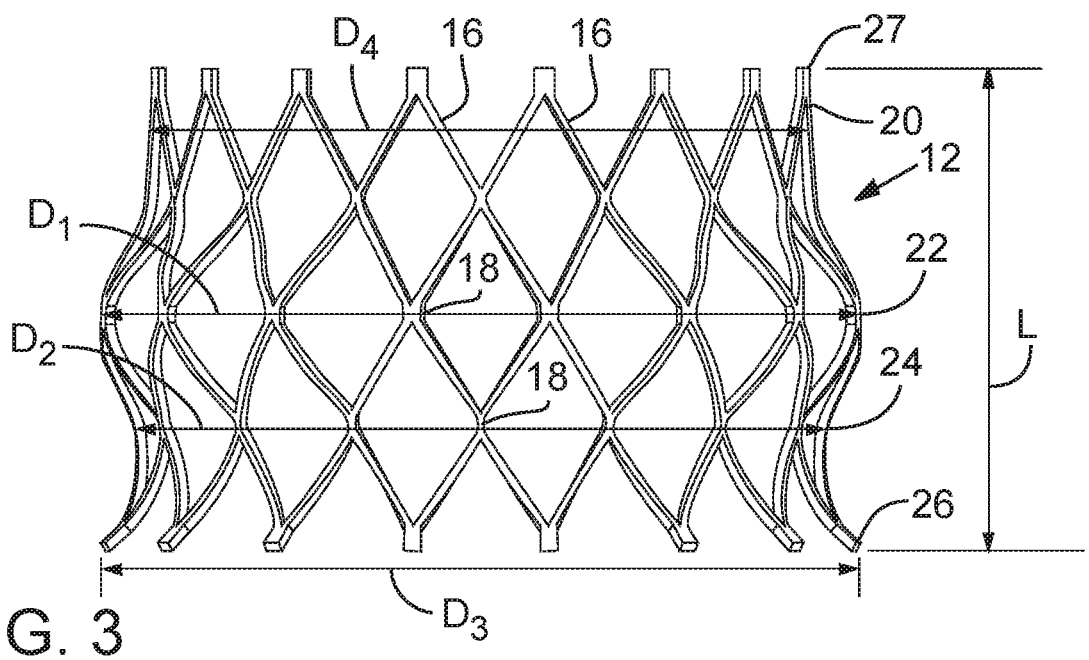
FIG. 3 is side elevation view of the support frame of the prosthetic valve of FIG. 1.
Figure 4:
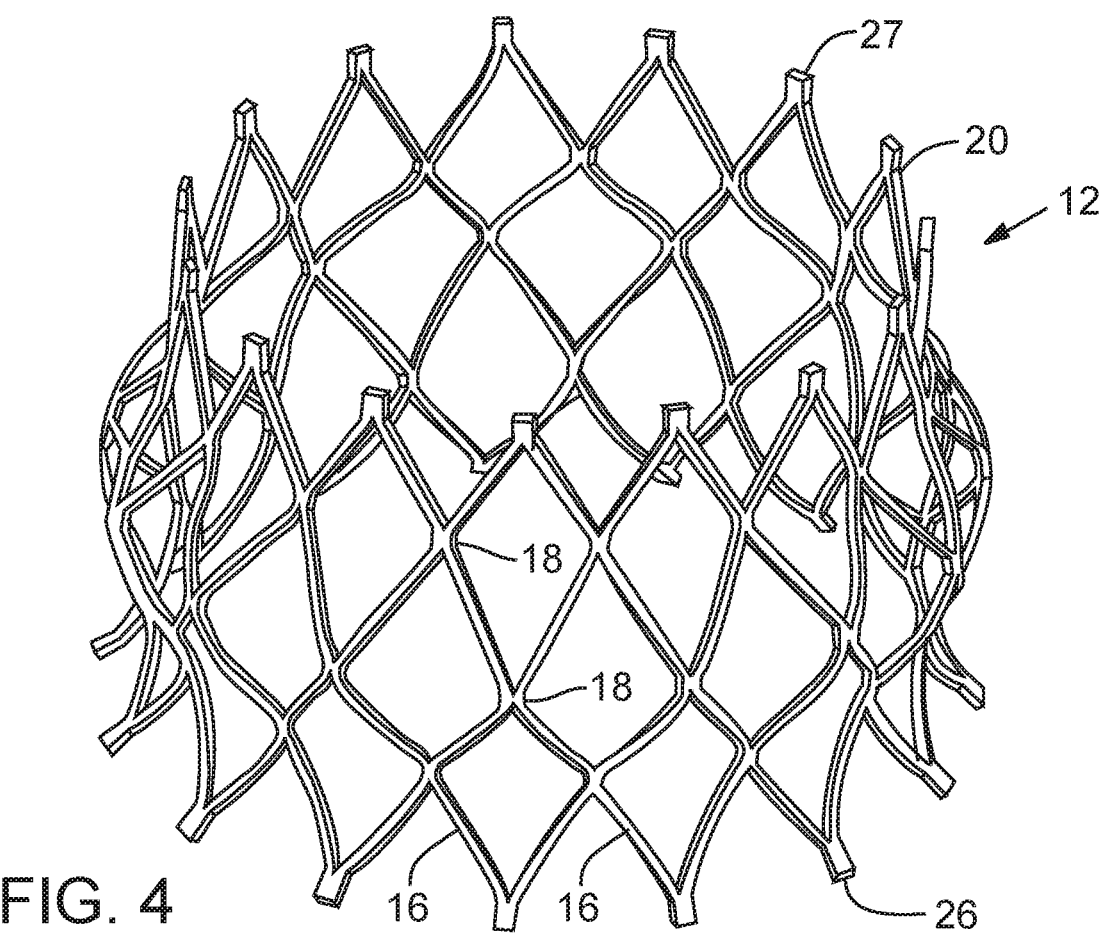
FIG. 4 is a perspective view of the support frame of the prosthetic valve of FIG. 1.

FIGS. 3 and 4 show the stent 12 without the leaflet section 14 for purposes of illustration. As shown, the stent 12 can be formed from a plurality of longitudinally extending, generally sinusoidal shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the prosthetic valve to be compressed to a reduced diameter for delivery in a delivery apparatus (such as described below) and then causes the prosthetic valve to expand to its functional size inside the patient's body when deployed from the delivery apparatus. If the prosthetic valve is a balloon-expandable prosthetic valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the Valsalva sinuses in the root of the aorta to assist in anchoring the prosthetic valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

Figure 5A:
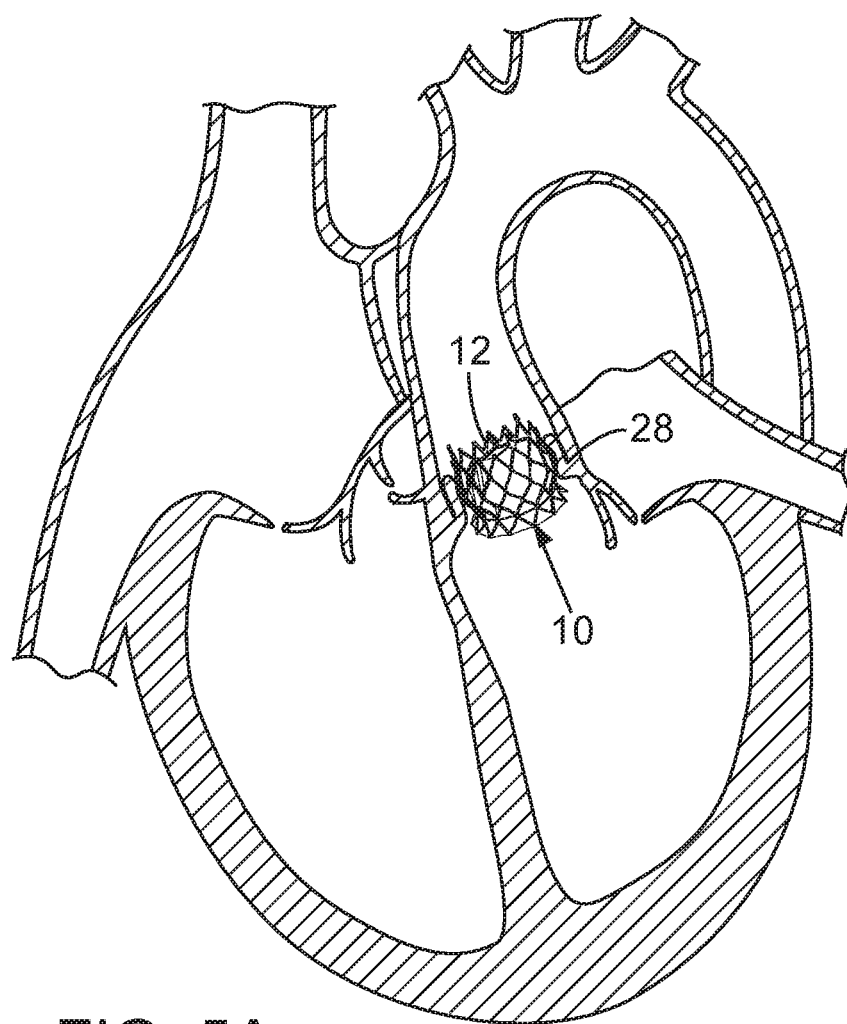
FIG. 5A is a cross-sectional view of the heart showing the prosthetic valve of FIG. 1 implanted within the aortic annulus.
Figure 5B:
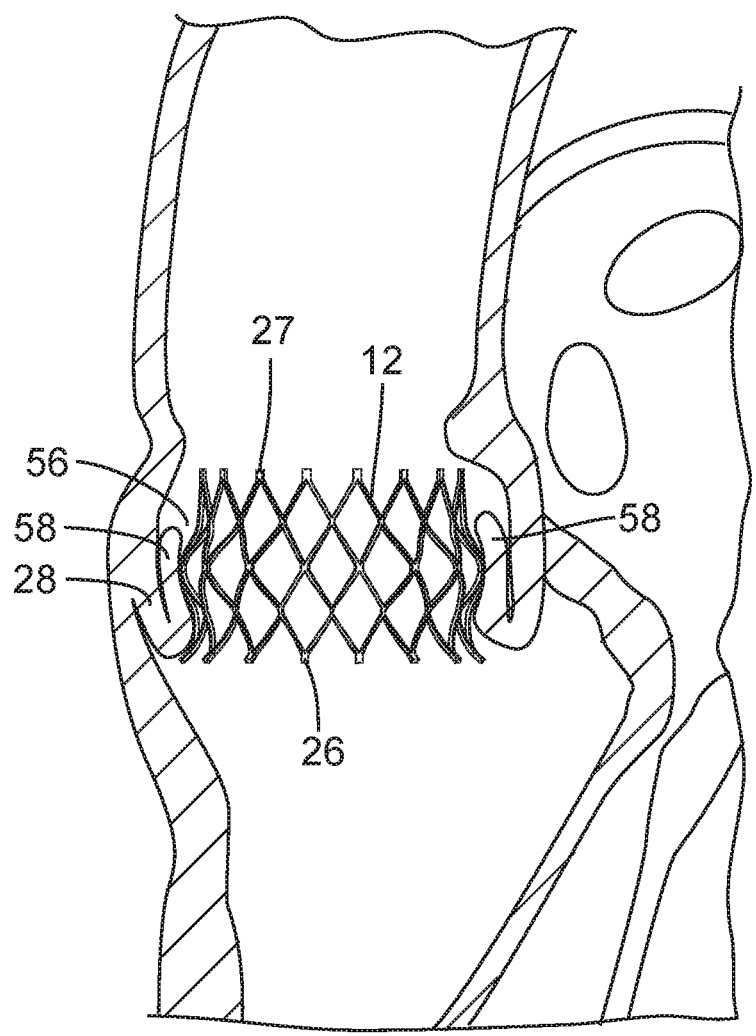
FIG. 5B is an enlarged view of FIG. 5A illustrating the prosthetic valve implanted within the aortic annulus, shown with the leaflet structure of the prosthetic valve removed for clarity.

When the prosthetic valve is in its expanded state, the intermediate section 22 has a diameter $D_1$, the inflow end portion 24 has a minimum diameter $D_2$, the inflow end 26 has a diameter $D_3$, and the outflow end portion 20 has a diameter $D_4$, where $D_2$ is less than $D_1$ and $D_3$, and $D_4$ is less than $D_2$. In addition, $D_1$ and $D_3$ desirably are greater than the diameter of the native annulus in which the prosthetic valve is to be implanted. In this manner, the overall shape of the stent 12 assists in retaining the prosthetic valve at the implantation site. More specifically, and referring to FIGS. 5A and 5B, the prosthetic valve 10 can be implanted within a native valve (the aortic valve in the illustrated example) such that the lower section 24 is positioned within the aortic annulus 28, the intermediate section 24 extends above the aortic annulus into the Valsalva's sinuses 56, and the lower flared end 26 extends below the aortic annulus. The prosthetic valve 10 is retained within the native valve by the radial outward force of the lower section 24 against the surrounding tissue of the aortic annulus 28 as well as the geometry of the stent. Specifically, the intermediate section 24 and the flared lower end 26 extend radially outwardly beyond the aortic annulus 28 to better resist against axial dislodgement of the prosthetic valve in the upstream and downstream directions (toward and away from the aorta). Depending on the condition of the native leaflets 58, the prosthetic valve typically is deployed within the native annulus 28 with the native leaflets 58 folded upwardly and compressed between the outer surface of the stent 12 and the walls of the Valsalva sinuses, as depicted in FIG. 5B. In some cases, it may be desirable to excise the leaflets 58 prior to implanting the prosthetic valve 10.

Known prosthetic valves having a self-expanding frame typically have additional anchoring devices or frame portions that extend into and become fixed to non-diseased areas of the vasculature. Because the shape of the stent 12 assists in retaining the prosthetic valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the native valve. Furthermore, a shorter prosthetic valve is more easily navigated around the aortic arch.

In particular embodiments, for a prosthetic valve intended for use in a 22-mm to 24-mm annulus, the diameter $D_1$ is about 28 mm to about 32 mm, with 30 mm being a specific example; the diameter $D_2$ is about 24 mm to about 28 mm, with 26 mm being a specific example; the diameter $D_3$ is about 28 mm to about 32 mm, with 30 mm being a specific example; and the diameter $D_4$ is about 24 mm to about 28 mm, with 26 mm being a specific example. The length L in particular embodiments is about 20 mm to about 24 mm, with 22 mm being a specific example.

Referring to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the prosthetic valve and a delivery apparatus (described below). In alternative embodiments, the retaining arms 30 need not be provided if a valve-retaining mechanism is not used.

Figure 6:
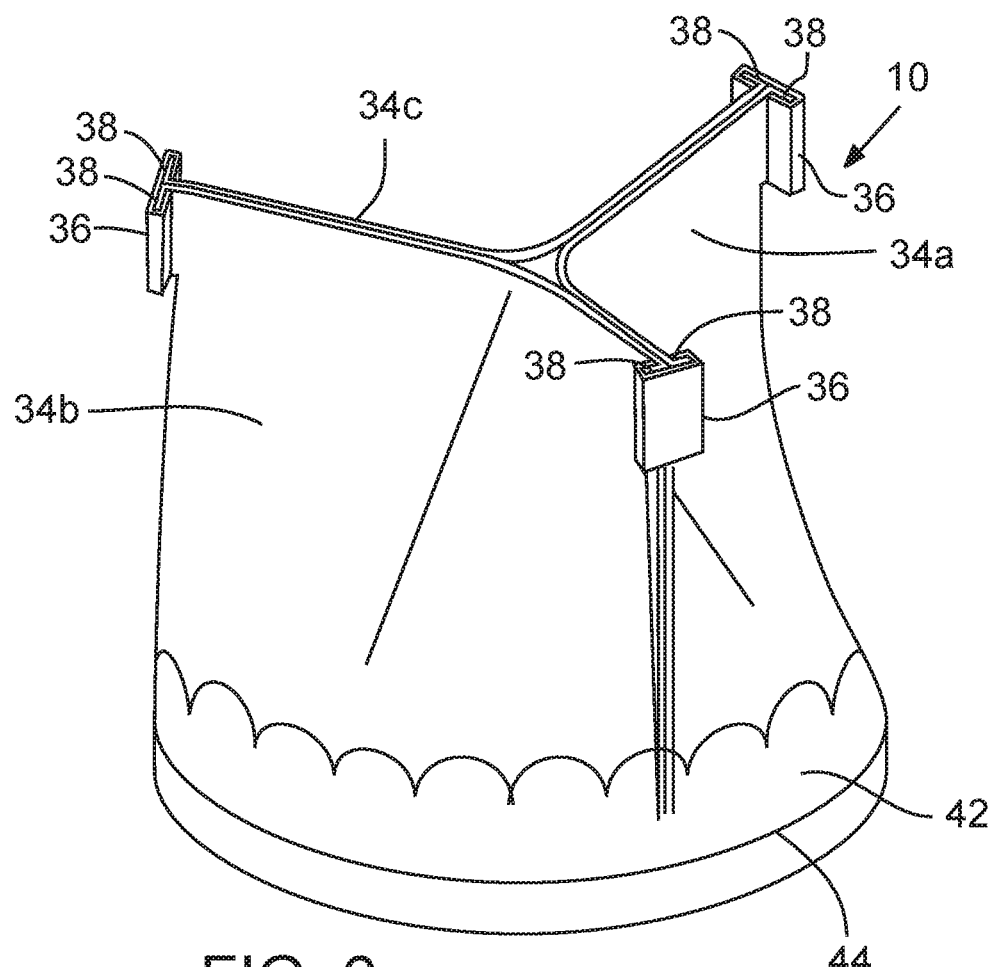
FIG. 6 is a perspective view of the leaflet structure of the prosthetic valve of FIG. 1 shown prior to being secured to the support frame.
Figure 7:
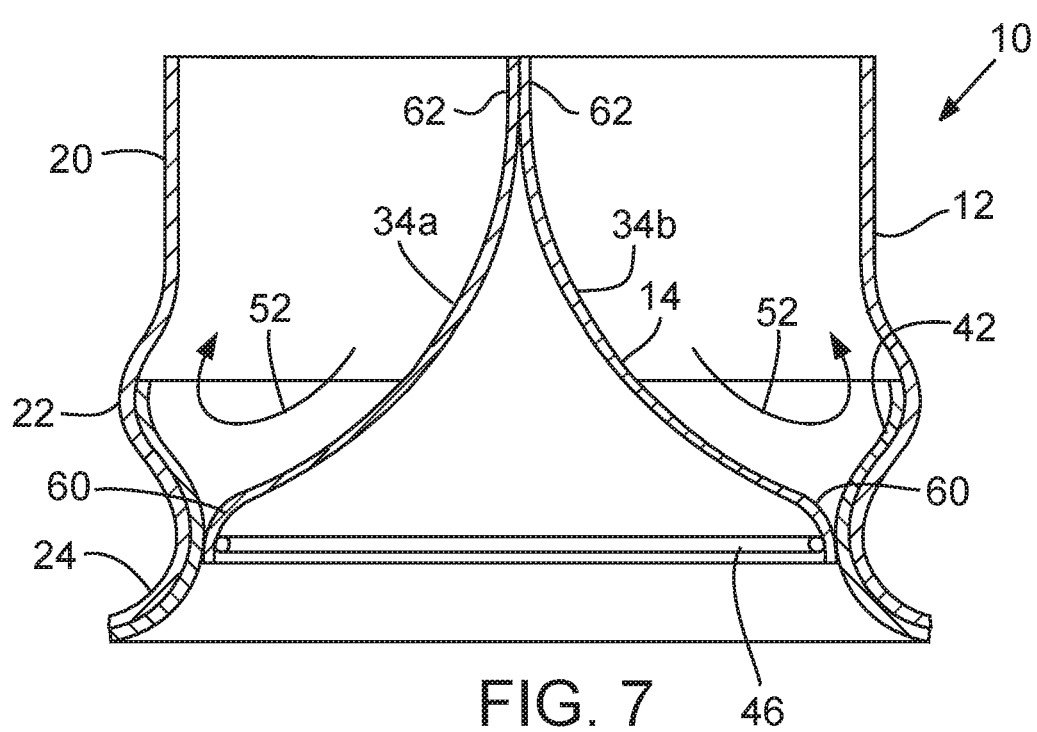
FIG. 7 is a cross-sectional view of the prosthetic valve of FIG. 1.

As best shown in FIGS. 6 and 7, the leaflet assembly 14 in the illustrated embodiment comprises three leaflets 34a, 34b, 34c made of a flexible material. Each leaflet has an inflow end portion 60 and an outflow end portion 62. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 14 can include an annular reinforcing skirt 42 that is secured to the outer surfaces of the inflow end portions of the leaflets 34a, 34b, 34c at a suture line 44 adjacent the inflow end of the prosthetic valve. The inflow end portion of the leaflet assembly 14 can be secured to the stent 12 by suturing the skirt 42 to struts 16 of the lower section 24 of the stent (best shown in FIG. 1). As shown in FIG. 7, the leaflet assembly 14 can further include an inner reinforcing strip 46 that is secured to the inner surfaces of the inflow end portions 60 of the leaflets.

Figure 2:
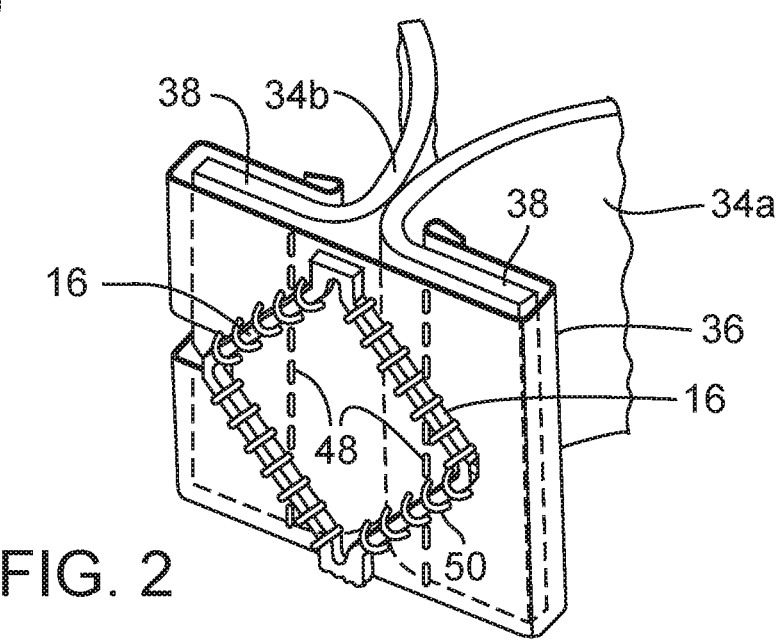
FIG. 2 is a perspective view of a portion of the prosthetic valve of FIG. 1 illustrating the connection of two leaflets to the support frame of the prosthetic valve.

Referring to FIGS. 1 and 2, the outflow end portion of the leaflet assembly 14 can be secured to the upper portion of the stent 12 at three angularly spaced commissure attachments of the leaflets 34a, 34b, 34c. As best shown in FIG. 2, each commissure attachment can be formed by wrapping a reinforcing section 36 around adjacent upper edge portions 38 of a pair of leaflets at the commissure formed by the two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end of the stent. The leaflets therefore desirably extend the entire length or substantially the entire length of the stent from the inflow end 26 to the outflow end 27. The reinforcing sections 36 reinforces the attachment of the leaflets to the stent so as to minimize stress concentrations at the suture lines and avoid "needle holes" on the portions of the leaflets that flex during use. The reinforcing sections 36, the skirt 42, and the inner reinforcing strip 46 desirably are made of a bio-compatible synthetic material, such as polytetrafluoroethylene (PTFE), or a woven fabric material, such as woven polyester (e.g., polyethylene terephtalate) (PET)).

FIG. 7 shows the operation of the prosthetic valve 10. During diastole, the leaflets 34a, 34b, 34c collapse to effectively close the prosthetic valve. As shown, the curved shape of the intermediate section 22 of the stent 12 defines a space between the intermediate section and the leaflets that mimics the Valsalva sinuses. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize clot formation.

The prosthetic valve 10 can be implanted in a retrograde approach where the prosthetic valve, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

FIGS. 8 and 9 show a delivery apparatus 100, according to one embodiment, that can be used to deliver a self-expanding prosthetic valve, such as prosthetic valve 10 described above, through a patient's vasculature. The delivery apparatus 100 comprises a first, outermost or main catheter 102 (shown alone in FIG. 10) having an elongated shaft 104, the distal end of which is coupled to a delivery sheath 106 (FIG. 18; also referred to as a delivery cylinder). The proximal end of the main catheter 102 is connected to a handle of the delivery apparatus. FIGS. 23-26 show an embodiment of a handle mechanism having an electric motor for operating the delivery apparatus. The handle mechanism is described in detail below. During delivery of a prosthetic valve, the handle can be used by a surgeon to advance and retract the delivery apparatus through the patient's vasculature. Although not required, the main catheter 102 can comprise a guide catheter that is configured to allow a surgeon to guide or control the amount the bending or flexing of a distal portion of the shaft 104 as it is advanced through the patient's vasculature, such as further described below. Another embodiment of a guide catheter is disclosed in U.S. Patent Publication No. 2008/0065011, which is incorporated herein by reference.

As best shown in FIG. 9, the delivery apparatus 100 also includes a second, intermediate catheter 108 (also referred to herein as a torque shaft catheter) having an elongated shaft 110 (also referred to herein as a torque shaft) and an elongated screw 112 connected to the distal end of the shaft 110. The shaft 110 of the intermediate catheter 108 extends coaxially through the shaft 104 of the main catheter 102. The delivery apparatus 100 can also include a third, nose-cone catheter 118 having an elongated shaft 120 and a nose piece, or nose cone, 122 secured to the distal end portion of the shaft 120. The nose piece 122 can have a tapered outer surface as shown for atraumatic tracking through the patient's vasculature. The shaft 120 of the nose-cone catheter extends through the prosthetic valve 10 (not shown in FIGS. 8-9) and the shaft 110 of the intermediate catheter 108. In the illustrated configuration, the innermost shaft 120 is configured to be moveable axially and rotatably relative to the shafts 104, 110, and the torque shaft 110 is configured to be rotatable relative to the shafts 104, 120 to effect valve deployment and release of the prosthetic valve from the delivery apparatus, as described in detail below. Additionally, the innermost shaft 120 can have a lumen for receiving a guide wire so that the delivery apparatus can be advanced over the guide wire inside the patient's vasculature.

As best shown in FIG. 10, the outer catheter 102 can comprise a flex control mechanism 168 at a proximal end thereof to control the amount the bending or flexing of a distal portion of the outer shaft 104 as it is advanced through the patient's vasculature, such as further described below.

The outer shaft 104 can comprise a proximal segment 166 that extends from the flex control mechanism 168 and a distal segment 126 that comprises a slotted metal tube that increases the flexibility of the outer shaft at this location. The distal end portion of the distal segment 126 can comprises an outer fork 130 of a valve-retaining mechanism 114 that is configured to releasably secure a prosthetic valve 10 to the delivery apparatus 100 during valve delivery, as described in detail below.

FIG. 28A is an enlarged view of a portion of the distal segment 126 of the outer shaft 104. FIG. 28B shows the cut pattern that can be used to form the distal segment 126 by laser cutting the pattern in a metal tube. The distal segment 126 comprises a plurality of interconnected circular bands or links 160 forming a slotted metal tube. A pull wire 162 can be positioned inside the distal segment 126 and can extend from a location 164 of the distal segment 126 (FIGS. 10 and 12) to the flex control mechanism. The distal end of the pull wire 162 can be secured to the inner surface of the distal segment 126 at location 164, such as by welding. The proximal end of the pull wire 162 can be operatively connected to the flex control mechanism 168, which is configured to apply and release tension to the pull wire in order to control bending of the shaft, as further described below. The links 160 of the shaft and the gaps between adjacent links are shaped to allow bending of the shaft upon application of light pulling force on the pull wire 162. In the illustrated embodiment, as best shown in FIG. 12, the distal segment 126 is secured to a proximal segment 166 having a different construction (e.g., one or more layers of polymeric tubing). In the illustrated embodiment, the proximal segment 166 extends from the flex control mechanism 168 to the distal segment 126 and therefore makes up the majority of the length of the outer shaft 104. In alternative embodiments, the entire length or substantially the entire length of the outer shaft 104 can be formed from a slotted metal tube comprising one or more sections of interconnected links 160. In any case, the use of a main shaft having such a construction can allow the delivery apparatus to be highly steerable, especially when use in combination with a torque shaft having the construction shown in FIGS. 40 and 41 (described below).

The width of the links 160 can be varied to vary the flexibility of the distal segment along its length. For example, the links within the distal end portion of the slotted tube can be relatively narrower to increase the flexibility of the shaft at that location while the links within the proximal end portion of the slotted tube can be relatively wider so that the shaft is relatively less flexible at that location.

FIG. 29A shows an alternative embodiment of a distal segment, indicated at 126', which can be formed, for example, by laser cutting a metal tube. The segment 126' can comprise the distal segment of an outer shaft of a delivery apparatus (as shown in FIG. 12) or substantially the entire length of an outer shaft can have the construction shown in FIG. 29A. FIG. 29B shows the cut pattern for forming the segment 126'. In another embodiment, a delivery apparatus can include a composite outer shaft comprising a laser-cut metal tube laminated with a polymeric outer layer that is fused within the gaps in the metal layer. In one example, a composite shaft can comprise a laser cut metal tube having the cut pattern of FIGS. 29A and 29B and a polymeric outer layer fused in the gaps between the links 160 of the metal tube. In another example, a composite shaft can comprise a laser cut metal tube having the cut pattern of FIGS. 28A and 28B and a polymeric outer layer fused in the gaps between the links 160 of the metal tube. A composite shaft also can include a polymeric inner layer fused in the gaps between the links 160 of the metal tube.

Referring to FIGS. 8A and 11, the flex control mechanism 168 can comprise a rotatable housing, or handle portion, 186 that houses a slide nut 188 mounted on a rail 192. The slide nut 188 is prevented from rotating within the housing by one or more rods 192, each of which is partially disposed in a corresponding recess within the rail 192 and a slot or recess on the inside of the nut 188. The proximal end of the pull wire 162 is secured to the nut 188. The nut 188 has external threads that engage internal threads of the housing. Thus, rotating the housing 186 causes the nut 188 to move axially within the housing in the proximal or distal direction, depending on the direction of rotation of the housing. Rotating the housing in a first direction (e.g., clockwise), causes the nut to travel in the proximal direction, which applies tension to the pull wire 162, which causes the distal end of the delivery apparatus to bend or flex. Rotating the housing in a second direction (e.g., counterclockwise), causes the nut to travel in the distal direction, which relieves tension in the pull wire 162 and allows the distal end of the delivery apparatus to flex back to its pre-flexed configuration under its own resiliency.

As best shown in FIG. 13, the torque shaft catheter 108 includes an annular projection in the form of a ring 128 (also referred to as an anchoring disc) mounted on the distal end portion of the torque shaft 110 adjacent the screw 112. The ring 128 is secured to the outer surface of the torque shaft 110 such that it cannot move axially or rotationally relative to the torque shaft. The inner surface of the outer shaft 104 is formed with a feature, such as a slot or recess, that receives the ring 128 in such a manner that the ring and the corresponding feature on the inner surface of the outer shaft 104 allow the torque shaft 110 to rotate relative to the outer shaft 104 but prevent the torque shaft from moving axially relative to the outer shaft. The corresponding feature on the outer shaft 104 that receives the ring 128 can be inwardly extending tab portions formed in the distal segment 126, such as shown at 164 in FIG. 12. In the illustrated embodiment (as best shown in FIG. 14), the ring 128 is an integral part of the screw 112 (i.e., the screw 112 and the ring 128 are portions of single component). Alternatively, the screw 112 and the ring are separately formed components but are both fixedly secured to the distal end of the torque shaft 110.

The torque shaft 110 desirably is configured to be rotatable relative to the delivery sheath 106 to effect incremental and controlled advancement of the prosthetic valve 10 from the delivery sheath 106. To such ends, and according to one embodiment, the delivery apparatus 100 can include a sheath retaining ring in the form of a threaded nut 150 mounted on the external threads of the screw 112. As best shown in FIG. 16, the nut 150 includes internal threads 152 that engage the external threads of the screw and axially extending legs 154. Each leg 154 has a raised distal end portion that extends into and/or forms a snap fit connection with openings 172 in the proximal end of the sheath 106 (as best shown in FIG. 18) so as to secure the sheath 106 to the nut 150. As illustrated in FIGS. 17B and 18, the sheath 106 extends over the prosthetic valve 10 and retains the prosthetic valve in a radially compressed state until the sheath 106 is retracted by the user to deploy the prosthetic valve.

As best shown in FIGS. 21 and 22, the outer fork 130 of the valve-retaining mechanism comprises a plurality of prongs 134, each of which extends through a region defined between two adjacent legs 154 of the nut so as to prevent rotation of the nut relative to the screw 112 upon rotation of the screw. As such, rotation of the torque shaft 110 (and thus the screw 112) causes corresponding axial movement of the nut 150. The connection between the nut 150 and the sheath 106 is configured such that axially movement of the nut along the screw 112 (in the distal or proximal direction) causes the sheath 106 to move axially in the same direction relative to the screw and the valve-retaining mechanism. FIG. 21 shows the nut 150 in a distal position wherein the sheath 106 (not shown in FIG. 21) extends over and retains the prosthetic valve 10 in a compressed state for delivery. Movement of the nut 150 from the distal position (FIG. 21) to a proximal position (FIG. 22) causes the sheath 106 to move in the proximal direction, thereby deploying the prosthetic valve from the sheath 106. Rotation of the torque shaft 110 to effect axial movement of the sheath 106 can be accomplished with a motorized mechanism (such as shown in FIGS. 23-26 and described below) or by manually turning a crank or wheel.

FIG. 17 shows an enlarged view of the nose cone 122 secured to the distal end of the innermost shaft 120. The nose cone 122 in the illustrated embodiment includes a proximal end portion 174 that is sized to fit inside the distal end of the sheath 106. An intermediate section 176 of the nose cone is positioned immediately adjacent the end of the sheath in use and is formed with a plurality of longitudinal grooves, or recessed portions, 178. The diameter of the intermediate section 176 at its proximal end 180 desirably is slightly larger than the outer diameter of the sheath 106. The proximal end 180 can be held in close contact with the distal end of the sheath 106 to protect surrounding tissue from coming into contact with the metal edge of the sheath. The grooves 178 allow the intermediate section to be compressed radially as the delivery apparatus is advanced through an introducer sheath. This allows the nose cone to be slightly oversized relative to the inner diameter of the introducer sheath. FIG. 17B shows a cross-section the nose cone 122 and the sheath 106 in a delivery position with the prosthetic valve retained in a compressed delivery state inside the sheath 106 (for purposes of illustration, only the stent 12 of the prosthetic valve is shown). As shown, the proximal end 180 of the intermediate section 176 can abut the distal end of the sheath 106 and a tapered proximal surface 182 of the nose cone can extend within a distal portion of the stent 12.

As noted above, the delivery apparatus 100 can include a valve-retaining mechanism 114 (FIG. 8B) for releasably retaining a stent 12 of a prosthetic valve. The valve-retaining mechanism 114 can include a first valve-securement component in the form of an outer fork 130 (as best shown in FIG. 12) (also referred to as an "outer trident" or "release trident"), and a second valve-securement component in the form of an inner fork 132 (as best shown in FIG. 17) (also referred to as an "inner trident" or "locking trident"). The outer fork 130 cooperates with the inner fork 132 to form a releasable connection with the retaining arms 30 of the stent 12.

The proximal end of the outer fork 130 is connected to the distal segment 126 of the outer shaft 104 and the distal end of the outer fork is releasably connected to the stent 12. In the illustrated embodiment, the outer fork 130 and the distal segment 126 can be integrally formed as a single component (e.g., the outer fork and the distal segment can be laser cut or otherwise machined from a single piece of metal tubing), although these components can be separately formed and subsequently connected to each other. The inner fork 132 can be mounted on the nose catheter shaft 120 (as best shown in FIG. 17). The inner fork 132 connects the stent to the distal end portion of the nose catheter shaft 120. The nose catheter shaft 120 can be moved axially relative to the outer shaft 104 to release the prosthetic valve from the valve-retaining mechanism, as further described below.

As best shown in FIG. 12, the outer fork 130 includes a plurality of angularly-spaced prongs 134 (three in the illustrated embodiment) corresponding to the retaining arms 30 of the stent 12, which prongs extend from the distal end of distal segment 126. The distal end portion of each prong 134 includes a respective opening 140. As best shown in FIG. 17, the inner fork 132 includes a plurality of angularly-spaced prongs 136 (three in the illustrated embodiment) corresponding to the retaining arms 30 of the stent 12, which prongs extend from a base portion 138 at the proximal end of the inner fork. The base portion 138 of the inner fork is fixedly secured to the nose catheter shaft 120 (e.g., with a suitable adhesive) to prevent axial and rotational movement of the inner fork relative to the nose catheter shaft 120.

Each prong of the outer fork cooperates with a corresponding prong of the inner fork to form a releasable connection with a retaining arm 30 of the stent. In the illustrated embodiment, for example, the distal end portion of each prong 134 is formed with an opening 140. When the prosthetic valve is secured to the delivery apparatus (as best shown in FIG. 19), each retaining arm 30 of the stent 12 extends inwardly through an opening 140 of a prong 134 of the outer fork and a prong 136 of the inner fork is inserted through the opening 32 of the retaining arm 30 so as to retain the retaining arm 30 from backing out of the opening 140. FIG. 42 also shows the prosthetic valve 10 secured to the delivery apparatus by the inner and outer forks before the prosthetic valve is loaded into the sheath 106. Retracting the inner prongs 136 proximally (in the direction of arrow 184 in FIG. 20) to remove the prongs from the openings 32 is effective to release the prosthetic valve 10 from the retaining mechanism. When the inner fork 132 is moved to a proximal position (FIG. 20), the retaining arms 30 of the stent can move radially outwardly from the openings 140 in the outer fork 130 under the resiliency of the stent. In this manner, the valve-retaining mechanism 114 forms a releasable connection with the prosthetic valve that is secure enough to retain the prosthetic valve relative to the delivery apparatus to allow the user to fine tune or adjust the position of the prosthetic valve after it is deployed from the delivery sheath. When the prosthetic valve is positioned at the desired implantation site, the connection between the prosthetic valve and the retaining mechanism can be released by retracting the nose catheter shaft 120 relative to the outer shaft 104 (which retracts the inner fork 132 relative to the outer fork 130).

Techniques for compressing and loading the prosthetic valve 10 into the sheath 106 are described below. Once the prosthetic valve 10 is loaded in the delivery sheath 106, the delivery apparatus 100 can be inserted into the patient's body for delivery of the prosthetic valve. In one approach, the prosthetic valve can be delivered in a retrograde procedure where delivery apparatus is inserted into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the prosthetic valve 10 is advanced to a location adjacent to or within the native aortic valve.

Thereafter, the prosthetic valve 10 can be deployed from the delivery apparatus 100 by rotating the torque shaft 110 relative to the outer shaft 104. As described below, the proximal end of the torque shaft 110 can be operatively connected to a manually rotatable handle portion or a motorized mechanism that allows the surgeon to effect rotation of the torque shaft 110 relative to the outer shaft 104. Rotation of the torque shaft 110 and the screw 112 causes the nut 150 and the sheath 106 to move in the proximal direction toward the outer shaft (FIG. 22), which deploys the prosthetic valve from the sheath. Rotation of the torque shaft 110 causes the sheath to move relative to the prosthetic valve in a precise and controlled manner as the prosthetic valve advances from the open distal end of the delivery sheath and begins to expand. Hence, unlike known delivery apparatuses, as the prosthetic valve begins to advance from the delivery sheath and expand, the prosthetic valve is held against uncontrolled movement from the sheath caused by the expansion force of the prosthetic valve against the distal end of the sheath. In addition, as the sheath 106 is retracted, the prosthetic valve 10 is retained in a stationary position relative to the ends of the inner shaft 120 and the outer shaft 104 by virtue of the valve-retaining mechanism 114. As such, the prosthetic valve 10 can be held stationary relative to the target location in the body as the sheath is retracted. Moreover, after the prosthetic valve is partially advanced from the sheath, it may be desirable to retract the prosthetic valve back into the sheath, for example, to reposition the prosthetic valve or to withdraw the prosthetic valve entirely from the body. The partially deployed prosthetic valve can be retracted back into the sheath by reversing the rotation of the torque shaft, which causes the sheath 106 to advance back over the prosthetic valve in the distal direction.

In known delivery devices, the surgeon must apply push-pull forces to the shaft and/or the sheath to unsheathe the prosthetic valve. It is therefore difficult to transmit forces to the distal end of the device without distorting the shaft (e.g., compressing or stretching the shaft axially), which in turn causes uncontrolled movement of the prosthetic valve during the unsheathing process. To mitigate this effect, the shaft and/or sheath can be made more rigid, which is undesirable because the device becomes harder to steer through the vasculature. In contrast, the manner of unsheathing the prosthetic valve described above eliminates the application of push-pull forces on the shaft, as required in known devices, so that relatively high and accurate forces can be applied to the distal end of the shaft without compromising the flexibility of the device. In certain embodiments, as much as 20 lbs. of force can be transmitted to the end of the torque shaft without adversely affecting the unsheathing process. In contrast, prior art devices utilizing push-pull mechanisms typically cannot exceed about 5 lbs. of force during the unsheathing process.

After the prosthetic valve 10 is advanced from the delivery sheath and expands to its functional size (the expanded prosthetic valve 10 secured to the delivery apparatus is depicted in FIG. 42), the prosthetic valve remains connected to the delivery apparatus via the retaining mechanism 114. Consequently, after the prosthetic valve is advanced from the delivery sheath, the surgeon can reposition the prosthetic valve relative to the desired implantation position in the native valve such as by moving the delivery apparatus in the proximal and distal directions or side to side, or rotating the delivery apparatus, which causes corresponding movement of the prosthetic valve. The retaining mechanism 114 desirably provides a connection between the prosthetic valve and the delivery apparatus that is secure and rigid enough to retain the position of the prosthetic valve relative to the delivery apparatus against the flow of the blood as the position of the prosthetic valve is adjusted relative to the desired implantation position in the native valve. Once the surgeon positions the prosthetic valve at the desired implantation position in the native valve, the connection between the prosthetic valve and the delivery apparatus can be released by retracting the innermost shaft 120 in the proximal direction relative to the outer shaft 104, which is effective to retract the inner fork 132 to withdraw its prongs 136 from the openings 32 in the retaining arms 30 of the prosthetic valve (FIG. 20). Slightly retracting of the outer shaft 104 allows the outer fork 130 to back off the retaining arms 30 of the prosthetic valve, which slide outwardly through openings 140 in the outer fork to completely disconnect the prosthetic valve from the retaining mechanism 114. Thereafter, the delivery apparatus can be withdrawn from the body, leaving the prosthetic aortic valve 10 implanted within the native valve (such as shown in FIGS. 5A and 5B).

The delivery apparatus 100 has at its distal end a semi-rigid segment comprised of relatively rigid components used to transform rotation of the torque shaft into axial movement of the sheath. In particular, this semi-rigid segment in the illustrated embodiment is comprised of the prosthetic valve and the screw 112. An advantage of the delivery apparatus 100 is that the overall length of the semi-rigid segment is minimized because the nut 150 is used rather than internal threads on the outer shaft to affect translation of the sheath. The reduced length of the semi-rigid segment increases the overall flexibility along the distal end portion of the delivery catheter. Moreover, the length and location of the semi-rigid segment remains constant because the torque shaft does not translate axially relative to the outer shaft. As such, the curved shape of the delivery catheter can be maintained during valve deployment, which improves the stability of the deployment. A further benefit of the delivery apparatus 100 is that the ring 128 prevents the transfer of axial loads (compression and tension) to the section of the torque shaft 110 that is distal to the ring.

In an alternative embodiment, the delivery apparatus can be adapted to deliver a balloon-expandable prosthetic valve. As described above, the valve retaining mechanism 114 can be used to secure the prosthetic valve to the end of the delivery apparatus. Since the stent of the prosthetic valve is not self-expanding, the sheath 106 can be optional. The retaining mechanism 114 enhances the pushability of the delivery apparatus and prosthetic valve assembly through an introducer sheath.

FIGS. 23-26 illustrate the proximal end portion of the delivery apparatus 100, according to one embodiment. The delivery apparatus 100 can comprise a handle 202 that is configured to be releasably connectable to the proximal end portion of a catheter assembly 204 comprising catheters 102, 108, 118. It may be desirable to disconnect the handle 202 from the catheter assembly 204 for various reasons. For example, disconnecting the handle can allow another device to be slid over the catheter assembly, such as a valve-retrieval device or a device to assist in steering the catheter assembly. It should be noted that any of the features of the handle 202 and the catheter assembly 204 can be implemented in any of the embodiments of the delivery apparatuses disclosed herein.

FIGS. 23 and 24 show the proximal end portion of the catheter assembly 204 partially inserted into a distal opening of the handle 202. The proximal end portion of the main shaft 104 is formed with an annular groove 212 (as best shown in FIG. 24) that cooperates with a holding mechanism, or latch mechanism, 214 inside the handle. When the proximal end portion of the catheter assembly is fully inserted into the handle, as shown in FIGS. 25 and 26, an engaging portion 216 of the holding mechanism 214 extends at least partially into the groove 212. One side of the holding mechanism 214 is connected to a button 218 that extends through the housing of the handle. The opposite side of the holding mechanism 214 is contacted by a spring 220 that biases the holding mechanism to a position engaging the main shaft 104 at the groove 212. The engagement of the holding mechanism 214 within the groove 212 prevents axial separation of the catheter assembly from the handle. The catheter assembly can be released from the handle by depressing button 218, which moves the holding mechanism 214 from locking engagement with the main shaft. Furthermore, the main shaft 104 can be formed with a flat surface portion within the groove 212. The flat surface portion is positioned against a corresponding flat surface portion of the engaging portion 216. This engagement holds the main shaft 104 stationary relative to the torque shaft 110 as the torque shaft is rotated during valve deployment.

The proximal end portion of the torque shaft 110 can have a driven nut 222 (FIG. 26) that is slidably received in a drive cylinder 224 (FIG. 25) mounted inside the handle. The nut 222 can be secured to the proximal end of the torque shaft 100 by securing the nut 222 over a coupling member 170 (FIG. 15). FIG. 26 is a perspective view of the inside of the handle 202 with the drive cylinder and other components removed to show the driven nut and other components positioned within the drive cylinder. The cylinder 224 has a through opening (or lumen) extending the length of the cylinder that is shaped to correspond to the flats of the nut 222 such that rotation of the drive cylinder is effective to rotate the nut 222 and the torque shaft 110. The drive cylinder can have an enlarged distal end portion 236 that can house one or more seals (e.g., O-rings 246) that form a seal with the outer surface of the main shaft 104 (FIG. 25). The handle can also house a fitting 238 that has a flush port in communication with the lumen of the torque shaft and/or the lumen of the main shaft.

The drive cylinder 224 is operatively connected to an electric motor 226 through gears 228 and 230. The handle can also house a battery compartment 232 that contains batteries for powering the motor 226. Rotation of the motor in one direction causes the torque shaft 110 to rotate, which in turn causes the sheath 106 to retract and uncover a prosthetic valve at the distal end of the catheter assembly. Rotation of the motor in the opposite direction causes the torque shaft to rotate in an opposite direction, which causes the sheath to move back over the prosthetic valve. An operator button 234 on the handle allows a user to activate the motor, which can be rotated in either direction to un-sheath a prosthetic valve or retrieve an expanded or partially expanded prosthetic valve.

As described above, the distal end portion of the nose catheter shaft 120 can be secured to an inner fork 132 that is moved relative to an outer fork 130 to release a prosthetic valve secured to the end of the delivery apparatus. Movement of the shaft 120 relative to the main shaft 104 (which secures the outer fork 130) can be effected by a proximal end portion 240 of the handle that is slidable relative to the main housing 244. The end portion 240 is operatively connected to the shaft 120 such that movement of the end portion 240 is effective to translate the shaft 120 axially relative to the main shaft 104 (causing a prosthetic valve to be released from the inner and outer forks). The end portion 240 can have flexible side panels 242 on opposite sides of the handle that are normally biased outwardly in a locked position to retain the end portion relative to the main housing 244. During deployment of the prosthetic valve, the user can depress the side panels 242, which disengage from corresponding features in the housing and allow the end portion 240 to be pulled proximally relative to the main housing, which causes corresponding axial movement of the shaft 120 relative to the main shaft. Proximal movement of the shaft 120 causes the prongs 136 of the inner fork 132 to disengage from the apertures 32 in the stent 12, which in turn allows the retaining arms 30 of the stent to deflect radially outwardly from the openings 140 in the prongs 134 of the outer fork 130, thereby releasing the prosthetic valve.

FIG. 27 shows an alternative embodiment of a motor, indicated at 400, that can be used to drive a torque shaft (e.g., torque shaft 110). In this embodiment, a catheter assembly can be connected directly to one end of a shaft 402 of the motor, without gearing. The shaft 402 includes a lumen that allows for passage of an innermost shaft (e.g., shaft 120) of the catheter assembly, a guide wire, and/or fluids for flushing the lumens of the catheter assembly.

Alternatively, the power source for rotating the torque shaft 110 can be a hydraulic power source (e.g., hydraulic pump) or pneumatic (air-operated) power source that is configured to rotate the torque shaft. In another embodiment, the handle can have a manually movable lever or wheel that is operable to rotate the torque shaft 110.

In another embodiment, a power source (e.g., an electric, hydraulic, or pneumatic power source) can be operatively connected to a shaft, which is turn is connected to a prosthetic valve 10. The power source is configured to reciprocate the shaft longitudinally in the distal direction relative to a valve sheath in a precise and controlled manner in order to advance the prosthetic valve from the sheath. Alternatively, the power source can be operatively connected to the sheath in order to reciprocate the sheath longitudinally in the proximal direction relative to the prosthetic valve to deploy the prosthetic valve from the sheath.

Figure 44:
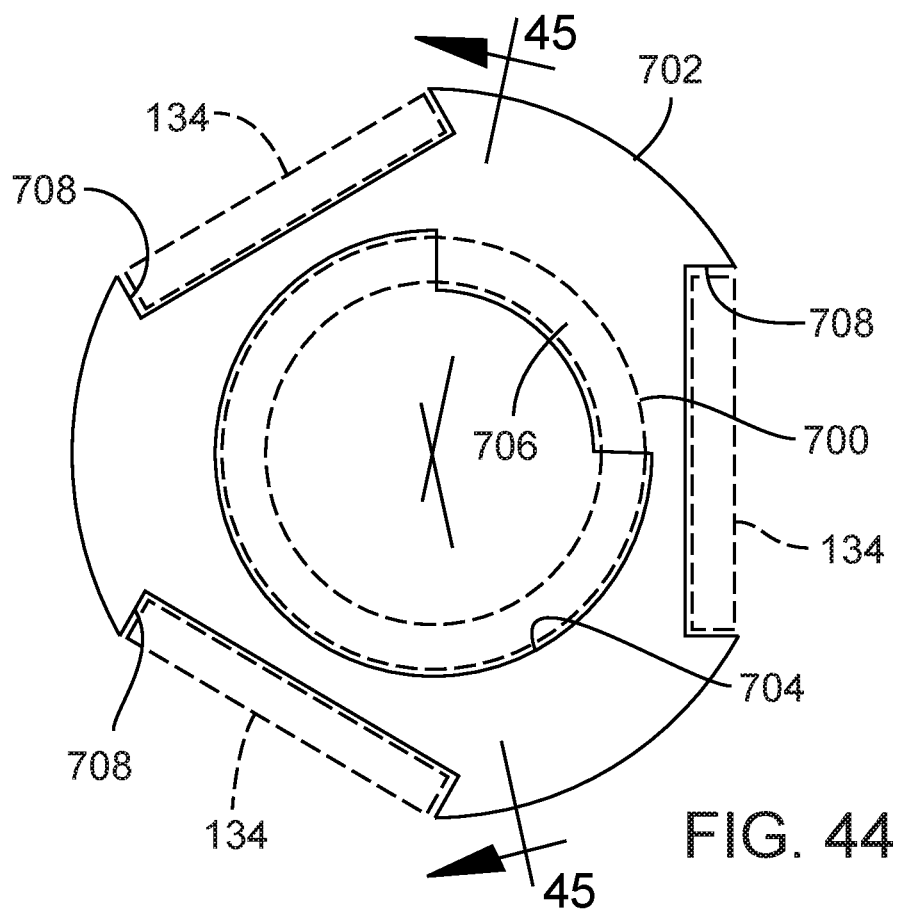
FIG. 44 is a front elevation view of a wire coil and washer assembly that can be incorporated in a torque shaft in place of the screw and nut assembly shown in FIG. 13 or the screw and nut assembly shown in FIG. 39A.
Figure 45:
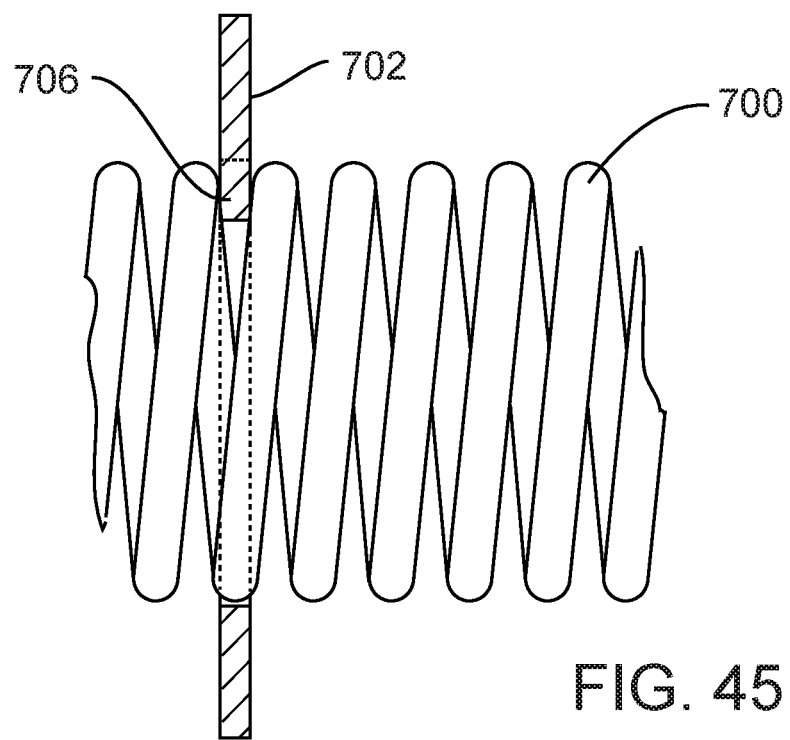
FIG. 45 is a side view of the wire coil and washer assembly of FIG. 44 shown partially in section.

FIGS. 44-45 show an alternative configuration for the screw 112 and nut 150 of the delivery apparatus 100 or delivery apparatus 600 (described below). In this embodiment, the screw 112 is replaced with a helical coil 700 (which can be, for example, a metal compression or tension spring), and the nut 150 is replaced with a sheath retaining ring in the form of a washer, or blade, 702 mounted on the coil 700. The proximal end of the coil is fixedly secured to the distal end of the torque shaft 110 (for example by welding or a suitable adhesive). The coil 700 can be made of any of various suitable metals (e.g., stainless steel, Nitinol, etc.) or polymeric materials.

The washer 702 has a central aperture 704 that receives the coil 700 and an internal tooth 706 that engages the grooves defined on the outer surface of the coil and desirably extends radially inwardly between adjacent turns or loops of the coil. The outer circumferential edge of the washer 702 can be formed with a plurality of recesses, or grooves, 708, each of which is sized to receive a prong 134 of the outer fork 130, which prevents rotation of the washer upon rotation of the torque shaft 110. The sheath 106 can be secured to the outer circumferential edge of the washer 702 in any convenient manner. For example, the portions between recesses 708 can extend into the openings 172 of the sheath (FIG. 18) to fix the sheath axially and rotationally relative to the washer. Alternatively, the washer can be welded or adhesively secured to the sheath.

When incorporated in the delivery apparatus 100, the coil 700 and washer 702 operate in a manner similar to the screw 112 and nut 150. Thus, when the torque shaft 110 is rotated, the washer 702 is caused to move axially along the length of the coil 700 to effect corresponding axial movement of the sheath, either to deploy a prosthetic valve or recapture a prosthetic valve back into the sheath. An advantage of the coil and washer configuration is that it allows the distal portion of the delivery apparatus occupied by the coil to bend or flex to facilitate tracking through the patient's vasculature, especially in patients with relatively small aortic arches and short ascending aortas. The coil also allows the sheath to be moved (proximally or distally) upon rotation of the torque shaft when the coil is in a flexed or curved state inside the patient's vasculature. In particular embodiments, the distal portion of the delivery apparatus occupied by the coil can be flexed from a straight configuration to a curved configuration having a radius of curvature of about 1 cm. In addition, the coil can change its pitch under dynamic loading (compression or tension), which reduces the build-up of tensile forces along the length of the delivery apparatus and avoids galling of the washer when subjected to bending forces.

The coil and washer configuration can be implemented in other delivery apparatuses that are used to implant various other types of prosthetic implants within body ducts. For example, the coil and washer configuration can be incorporated in a delivery apparatus used to implant stents or similar implants within the coronary sinus. The coil and washer configuration can also be utilized in various non-medical applications to replace a screw and nut assembly where the screw is subjected to bending forces.

Figure 30:
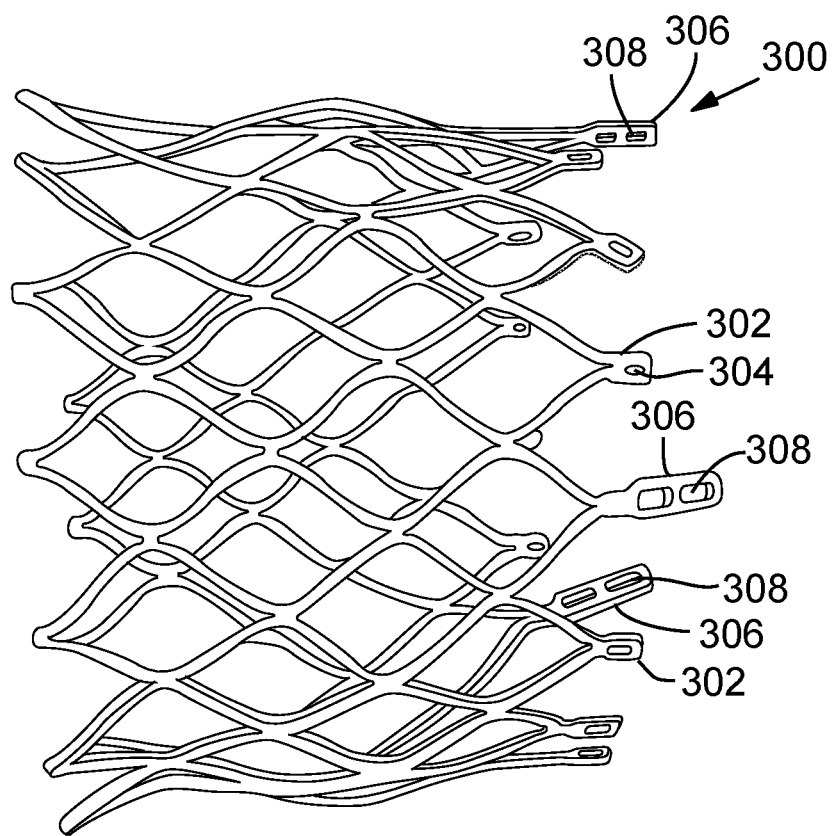
FIG. 30 is a side elevation view of a support stent for use in a prosthetic valve.

FIG. 30 shows another exemplary stent 300, for use in a prosthetic heart valve. For purposes of illustration, only the bare stent 300 is shown while the other components of the prosthetic valve, including the leaflets and the skirt, are omitted. However, it should be understood that the prosthetic valve can include leaflets 34a, 34b, 34c and a skirt 42 mounted to the stent 300, as described above in connection with the prosthetic valve 10. The stent 300 can have the same overall shape and configuration as the stent 12 of prosthetic valve 10 described above, except that all apices 302 at the outflow end of the stent 300 have respective apertures 304. The stent 300 can further comprise three commissure posts 306 (which are also referred to as "apices" herein) with eyelets 308, also at the outflow end. The delivery apparatuses 500, 600 (described below for use with stent 300) can be used to deliver the stent 10 (or any other stent with apices that lack apertures). In this case, the delivery apparatus can engage the stent by wrapping the suture loops around the apices at one end of the stent (e.g., the outflow end). In some embodiments, the stent can have notches, channels or other narrowed portions formed in or adjacent to the apices, for stably holding the suture loops against their respective apices.

Figure 31A:
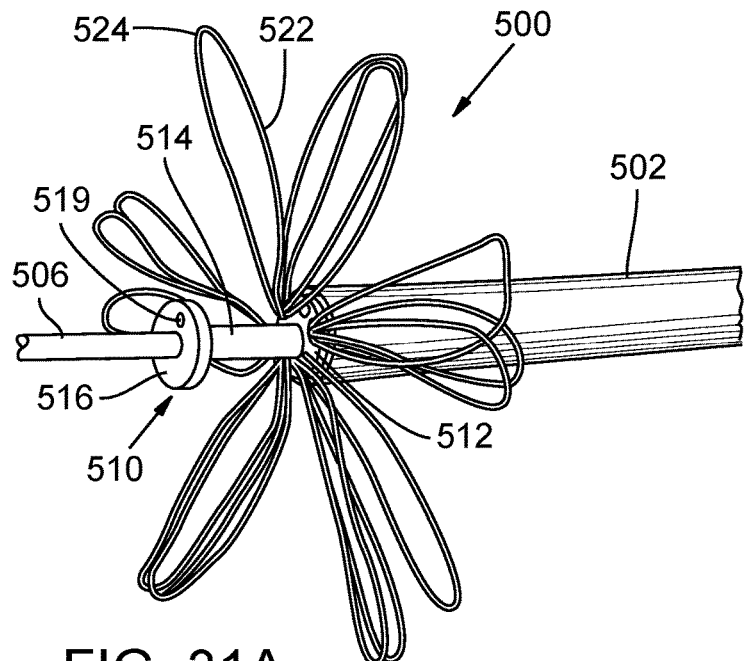
FIG. 31A is an enlarged view an exemplary delivery assembly having a plurality of suture loops for reversibly engaging the support stent of FIG. 30.

FIGS. 31A-37 show an exemplary delivery apparatus 500 for delivering the stent 300. The delivery apparatus 500 is similar to the delivery apparatus 100 except that the delivery apparatus 500 includes a different mechanism for releasably securing a prosthetic valve to the delivery apparatus. The delivery apparatus 500 in the illustrated embodiment comprises a main shaft 502, a sheath 504 mounted to the distal end of the shaft 502, an inner shaft 506 that extends co-axially through the main shaft 502, and a nose cone 508 mounted to the distal end of the inner shaft 506. The inner shaft 506 can have a guidewire lumen configured to receive a guidewire 509. As best shown in FIG. 31A, a suture-retention member 510 can extend distally from the distal end of the main shaft 502. The inner shaft 506 can extend co-axially through the suture-retention member 510.

Although not shown, the delivery apparatus 500 can also include a torque shaft that is effective to move the sheath 504 in the proximal and distal directions relative to the main shaft 502 and relative to a prosthetic valve secured to the distal end of the delivery apparatus. The distal end portion of the main shaft 502 can have the same configuration as the distal segment 126 of the shaft 104 of the delivery apparatus 100 described above.

Figure 32:
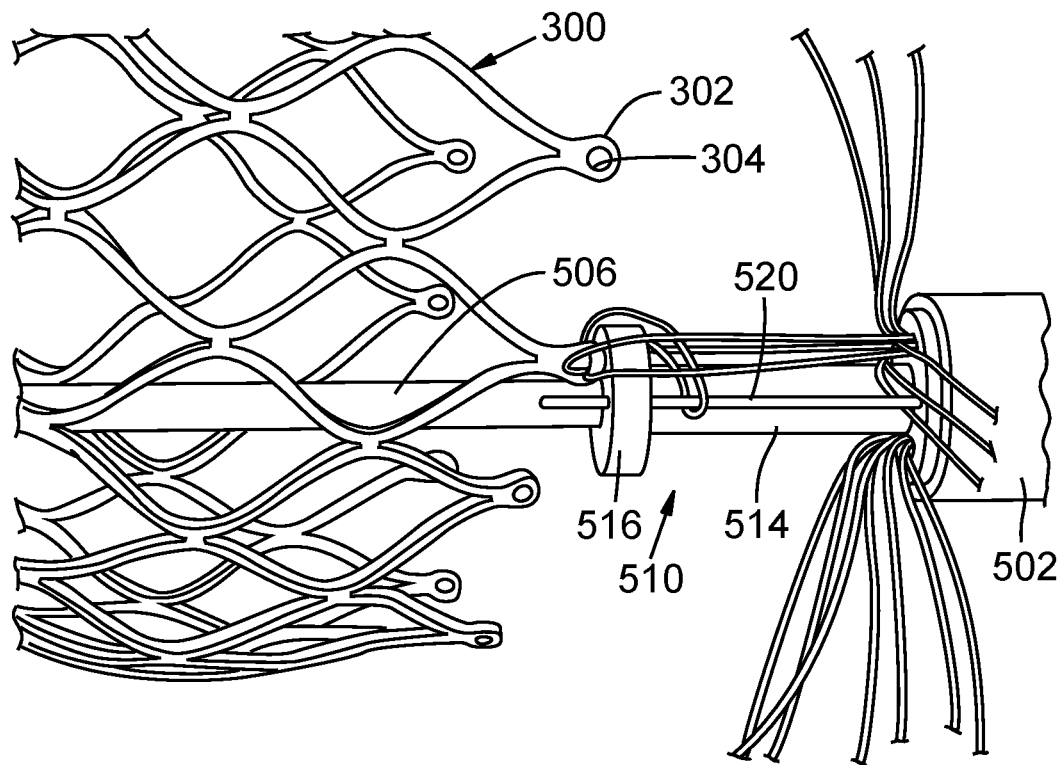
FIG. 32 is a side elevation view of an exemplary delivery assembly comprising the delivery catheter of FIG. 31A, with a suture loop shown engaging the stent of FIG. 30.
Figure 33:
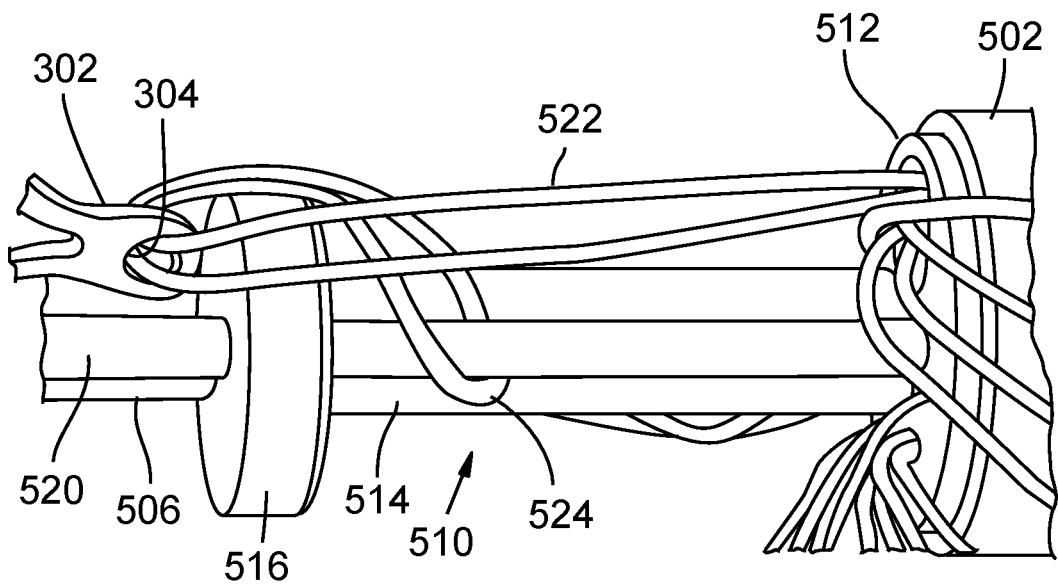
FIG. 33 is an enlarged view of the delivery assembly of FIG. 32 engaging the stent of FIG. 30.

The suture-retention member 510 comprises a proximal disc member 512, a distal disc member 516, and a shaft 514 extending between and connecting the proximal and distal disc members 512, 516, respectively. As best shown in FIG. 33, the proximal disc member 512 can be fixed inside of the main shaft 502. Each disc member 512, 516 is formed with one or more axially extending openings 518 (FIGS. 31C and 31D), each of which is sized to receive the distal end portion of a suture release member 520 (FIG. 32). The release member 520 can be, for example, a stiff wire, and therefore is referred to below as a release wire. In the illustrated embodiment, the delivery apparatus includes a single release wire 520 that extends distally through corresponding openings 518 in the disc members 512, 516 and proximally through the main shaft 502 along the length of the delivery apparatus toward a handle (not shown) of the delivery apparatus. The proximal end of the release wire (not shown) can be exposed at the proximal end of the delivery apparatus for being manipulated by a user or can be coupled to an actuator on the handle of the delivery apparatus that can control axial movement of the release wire.

The release wire 520 is slidable in the proximal and distal directions relative to the suture-retention member 510 to secure the stent 300 to the suture-retention member 510 via a plurality of suture loops 522 and to release the stent 300 from the suture-retention member, as further described below. In some embodiments, the delivery apparatus can include a plurality of such release wires 520 (such as two or three release wires 520), each of which extends through corresponding openings 518 in the disc members 512, 516. These release wires 520 can each interact with one or more suture loops 522, and can aid in balancing load distribution.

Figure 31B:
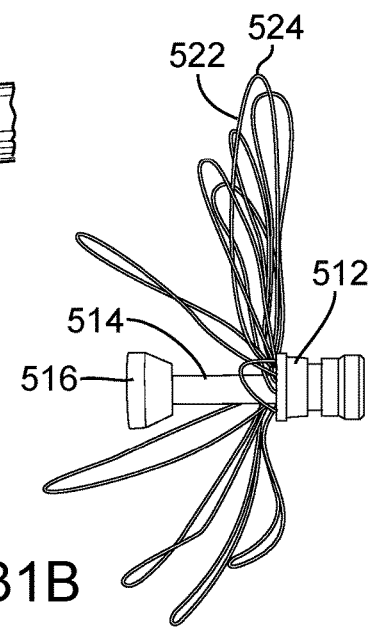
FIG. 31B is a side view of an exemplary suture-retention member for use in the delivery assembly of FIG. 31A.
Figure 31C:
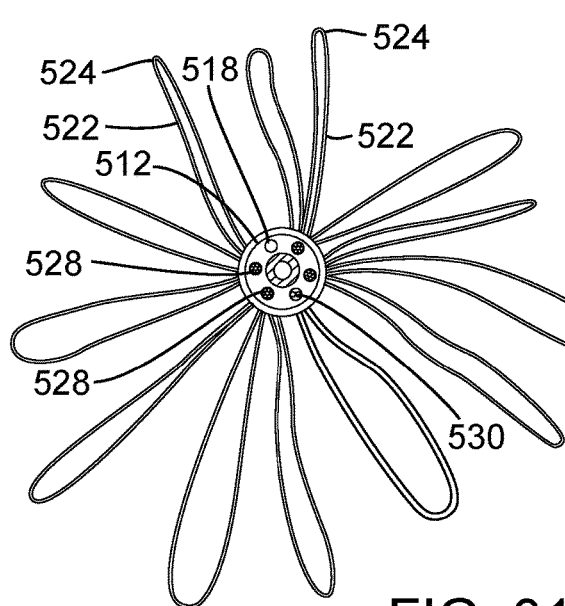
FIG. 31C is a proximal end view of the suture-retention member of FIG. 31B, showing a proximal end of a first (proximal) disc member with suture loops extending distally outward.

As noted above, the stent 300 can be releasably connected to the suture-retention member 510 using a plurality of suture loops 522. For that purpose, the proximal disc member 512 can include a plurality of openings 528 and 530 (in addition to opening 518 for the release wire) for threading the suture loops through the proximal disc member (FIGS. 31A and 31B). The suture loops 522 can be formed from a single piece of suture material that is folded multiple times so as to form multiple loops 522 extending distally from openings in the proximal disc member 512, as depicted in FIG. 31A. In alternative embodiments, each loop 522 can be formed from a separate piece of suture material. In some cases, each suture loop 522 consists entirely of a loop of suture material, whereas in other cases, one or more of the suture loops 522 can comprise a non-looped portion (such as a linear segment of suture material) proximal to the looped portion. As such, a "suture loop" can be characterized as "extending from" a given location, even if the looped portion itself does not originate or extend through that location, so long as the suture material comprising the looped portion extends from that location. However, where a "suture loop" is described as wrapping or extending around a given structure and/or residing at a given location, this specifically refers to the looped portion of the suture loop.

Figure 31D:
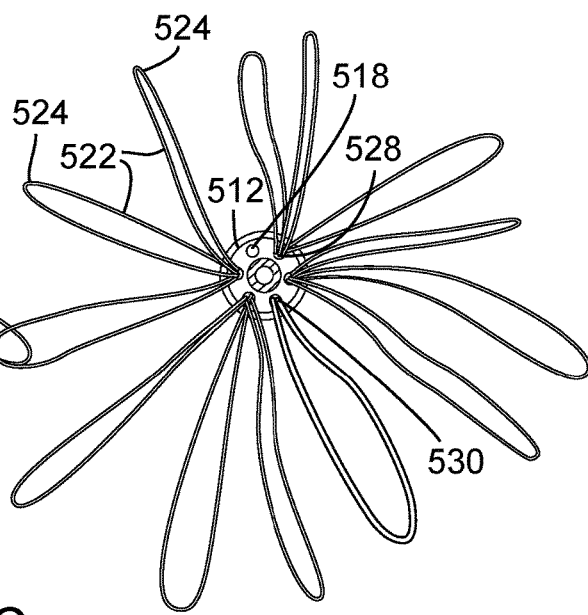
FIG. 31D, is a distal end view of the suture-retention member of FIG. 31B, showing a distal end view of the first disc member with suture loops extending distally outward. The second (distal) disc member and the shaft member of the suture-retention member are omitted from FIG. 31D for clarity.

As shown in FIGS. 31A-31D, multiple loops 522 (e.g., two or three loops) can extend outwardly from each opening in the proximal disc member 512, although in other embodiments each suture loop 522 can extend from a separate opening. As shown in FIG. 31D, the proximal disc member 512 can have six openings. Three suture loops 522 can extend from each of four openings 528 in the proximal disc member 512, and through apertures 304 in the apices 302. A fifth opening 530 can have one or more suture loops extending therefrom (such as three suture loops) to engage the commissure post eyelets 308 of the stent 300. Finally, the release wire 520 can extend distally from out of the sixth opening 518, toward the second disc member 516. In the illustrated embodiment, a single suture loop extends from the fifth opening 530 through the eyelets 308 of each of the commissure posts. In some cases, having a single suture loop extending through the commissure post eyelets 308 provides better tension control, resulting in more controlled release and/or recapture of the prosthetic valve. The suture loop(s) extending through the commissure post eyelets 308 may be thicker than the suture loops 522 that extend through the other stent apices 302. For example, in one embodiment, the suture loop(s) extending through the commissure posts are 4-0 sutures, whereas the suture loops extending through the apices are 3-0 sutures. The six openings can be arranged in an annular pattern as shown (FIG. 31D), and the suture loops 522 can be configured to extend outward to engage stent apices 302 in accordance with their relative positions within this annular pattern, such that the suture loops 522 do not cross past one another to reach their respective stent apices. In other embodiments, the suture loops can be configured to engage stent apices 302, such that the suture loops cross one another to reach respective stent apices.

Figure 34:
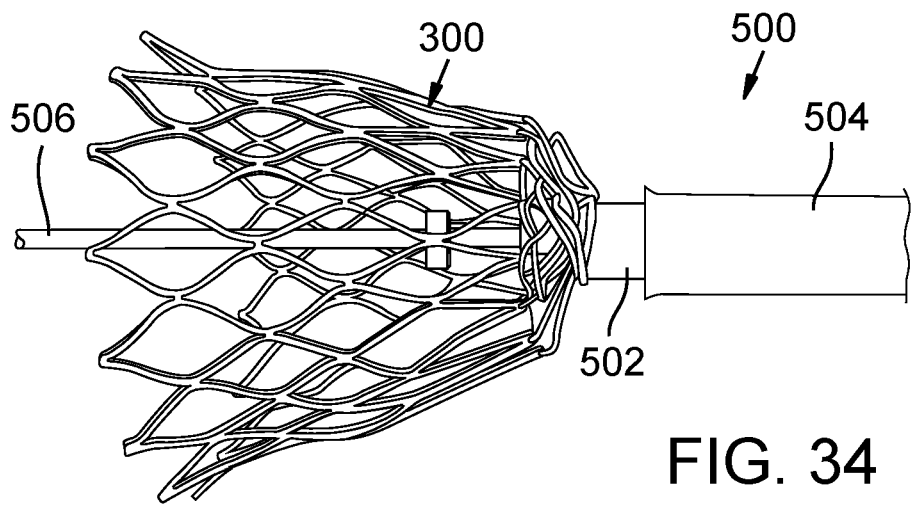
FIG. 34 is a side elevation view of the delivery assembly of FIG. 32 holding the stent of FIG. 30, with suture loops engaging each apex of the stent.

Referring to FIGS. 32 and 33, when loading the stent 300 onto the delivery apparatus, the apices 302 of the stent 300 are placed adjacent the distal disc member 516, and each suture loop 522 is threaded through a respective aperture 304 in one of the apices 302. By having a respective suture loop 522 extend through every apex 302 (including every commissure post 306), the prosthetic valve may be fully retrievable (while connected to the delivery apparatus), as the apices 302, 306 can be collapsed radially inward using the sutures 522. In certain embodiments, the functioning of the prosthetic valve can be assessed after deploying the valve from the sheath 504 and prior its recapture. In various embodiments, the number of apices and corresponding suture loops can vary, so long as a sufficient number of apices are connected such that the end of the prosthetic valve is collapsed when the apices are collapsed radially inward. In the embodiment shown, there are twelve suture loops threaded through twelve respective apices. The end 524 of each suture loop 522 is then placed in the area between the proximal and distal disc members 512, 516 and the release wire 520 is slid axially through the loop and a respective opening 519 in the distal disc member 516 (FIG. 31A) so as to retain the end 524 of the loop on the release wire, as depicted in FIG. 33. For purposes of illustration, FIGS. 32 and 33 show just a single suture loop 522 releasably connecting one of the apices 302 of the stent to the release wire 520. Desirably, a suture loop 522 is inserted through each of the apertures/eyelets 304, 308 in the apices 302, 306 of the stent and retained by the release wire 520. FIG. 34 shows the stent 300 after suture loops 522 are inserted through all of the apices of the stent and retained on the release wire 520. As noted above, while only one release wire 520 is shown in the illustrated embodiment, the delivery apparatus can be provided with a plurality of release wires 520 for retaining the suture loops 522.

When threading the suture loops 522 through the openings 304, 308 of the apices, the suture loops 522 can be threaded sequentially through each of the openings 304, 308 moving in a circumferential direction around the stent. In another embodiment, the suture loops 522 can be inserted through every second or third or fourth opening 304, 308 and placed on the release wire 520, moving in a circumferential direction around the stent several times until a suture loop is inserted through each of the openings, so as to balance the stent attachment relative to the release wire 520.

Figure 35:
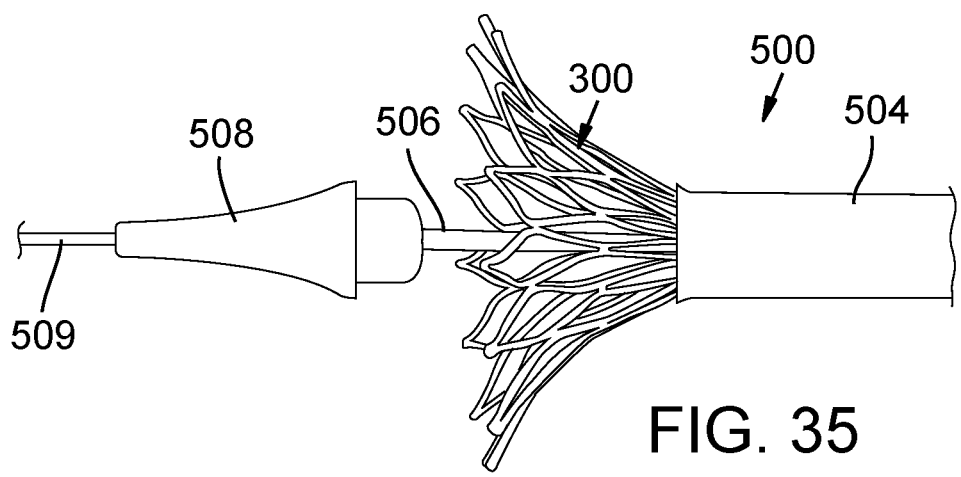
FIG. 35 is a side elevation view of the delivery assembly of FIG. 32, with a sheath component of the delivery assembly advanced over a portion of the stent of FIG. 30.
Figure 36:
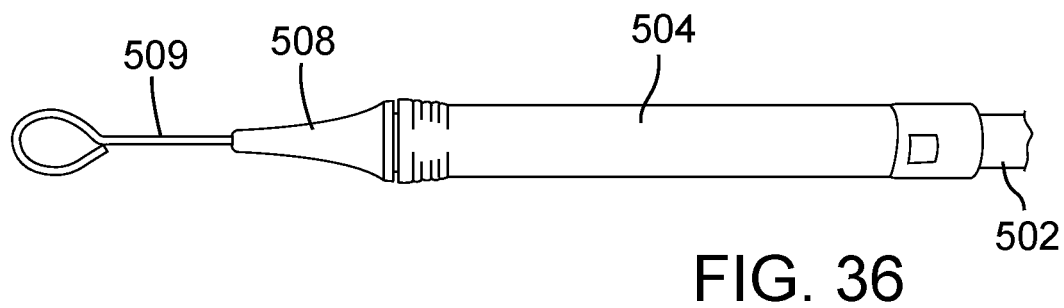
FIG. 36 is a side elevation view of the delivery assembly of FIG. 32, with a sheath component of the delivery assembly fully advanced over the stent of FIG. 30.

After the stent 300 is connected to the suture-retention member 510 (FIG. 34), the sheath 504 is advanced distally (e.g., by rotating the torque shaft of the delivery apparatus) to load the prosthetic valve into the sheath. As the sheath 504 is advanced over the suture loops 522, tension in the suture loops causes the apices 302, 306 to collapse radially inward toward the main shaft 502. The sheath 504 is further advanced, causing the sheath 504 to extend over and collapse the stent 300 (as shown in FIG. 35), until the distal end of the sheath 504 abuts the nose cone 508 (FIG. 36). As best shown in FIG. 33, the apices 302 can bear against the distal surface of the distal disc member 516, which prevents the prosthetic valve from sliding proximally and maintains tension in the suture loops 522 as the sheath is retracted.

Figure 37:
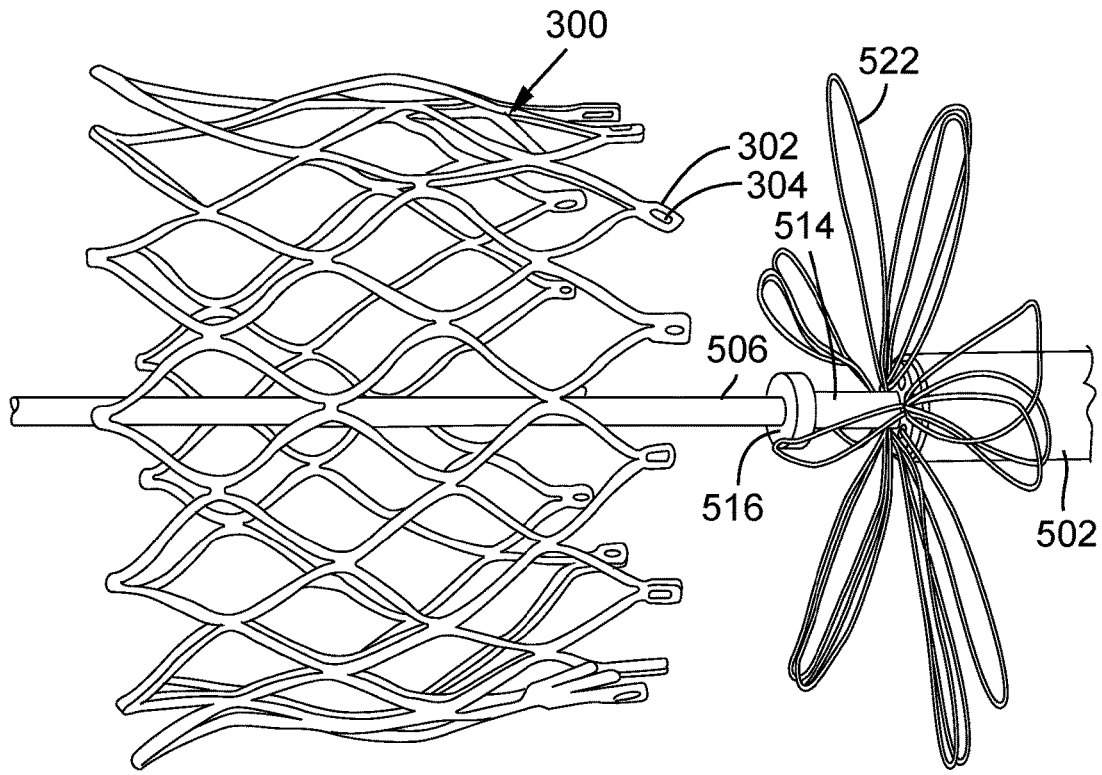
FIG. 37 is a side elevation view of the delivery catheter of FIG. 32, with suture loops disengaged from the stent of FIG. 30.
Figure 38:
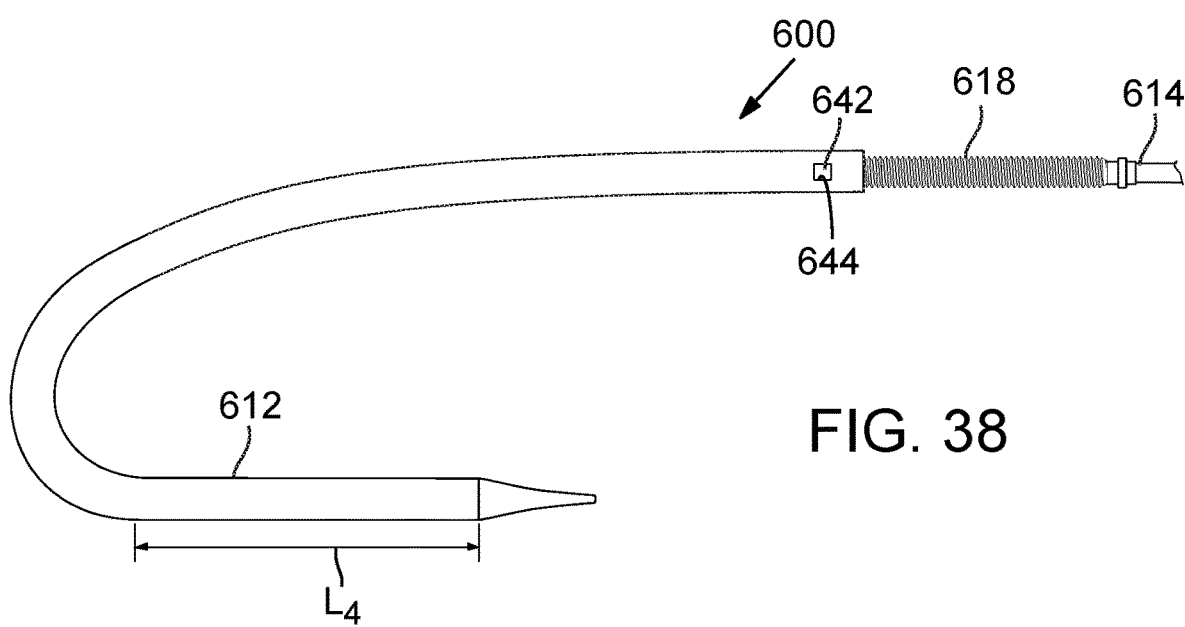
FIG. 38 is a top view of another exemplary delivery assembly, showing a delivery cylinder and a screw mechanism. The delivery assembly can have a single, continuous outer sleeve portion (not shown) covering the components.

When the prosthetic valve is delivered to the desired implantation site within the body, the sheath 504 is retracted (e.g., by rotating the toque shaft) to deploy the prosthetic valve. After the prosthetic valve is fully deployed from the sheath, the stent 300 is still connected to the stent-retention member 510 by the suture loops 522, as depicted in FIG. 34. Thus, if it becomes necessary to retrieve the prosthetic valve such as for removal or re-positioning, the sheath 504 is advanced distally to draw the prosthetic valve back into the sheath. On the other hand, if it is determined that the prosthetic valve is accurately positioned at the desired implantation site, the release wire 520 can be pulled proximally to release the ends 524 of the suture loops 522. Slight retraction of the main shaft 502 is effective to pull the suture loops out of the openings 302 in the stent 300, as depicted in FIG. 37. The proximal end of the release wire 520 can be exposed at the proximal end of the delivery apparatus so that the user can manually pull the release wire to release the prosthetic valve. Alternatively, the handle can have an actuator or switch that is configured to effect proximal movement of the release wire.

The sheath 504 can be made of a polymeric material, such as PEEK or nylon-12, and can have a reinforced distal tip portion, such as by securing a metal ring to the distal end portion of the sheath, to better resist the expansion force of the stent as it is drawn into the sheath. Alternatively, the sheath 504 can comprise a metal cylinder having a polymeric soft tip portion reflowed or molded to the distal end portion of the cylinder.

FIGS. 38-43 shows another delivery apparatus 600 generally comprising a first catheter 602 and a second catheter 604 extending coaxially through the first catheter 602, and a delivery sheath or cylinder 612 coupled to the distal ends of the catheters 602, 604. The proximal ends of the catheters 602, 604 can be coupled to a handle (e.g., a handle 202 such as shown in FIG. 23). As best shown in FIG. 40, the first catheter 602 comprises an elongated shaft 606 that extends distally from the handle, an intermediate section 608 extending distally from the distal end of the shaft 606, and a distal end portion 610 extending distally from the intermediate section 608. The intermediate section 608 comprises a plurality of angularly spaced rails 613 that extend longitudinally from the shaft 606 to the distal end portion 610. The rails 613 cooperate with a nut 640 to inhibit rotation of the nut yet allow longitudinal movement of the nut upon rotation of the second catheter 604. In this manner, the rails 613 serve the same purpose of the prongs 134 in preventing rotation of the nut 150. The distal end portion 610 in the illustrated embodiment comprises a slotted metal tube to enhance the flexibility of this section of the first catheter 602.

As best shown in FIGS. 39A-39C, the second catheter 604 can comprise a elongated shaft 614 (which can be referred to as a "torque shaft"), a coupling member 616 connected to the proximal end of the shaft 614, and a threaded screw 618 connected to the distal end of the shaft 614. The coupling member 616 is configured to be connected to a handle as described above (e.g., a handle 202). The screw 618 has external threads that engage internal threads of the nut 640. As best shown in FIG. 41, when the apparatus is assembled, the elongated shaft 614 of the second catheter 604 extends coaxially through the elongated shaft 606 of the first catheter 602, and the screw 618 extends coaxially through the railed section 608 of the first catheter 602. The nut 640 is mounted on the screw 618 and is connected to the proximal end portion of delivery cylinder 612. The distal end portion 610 of the first catheter 602 extends coaxially through the delivery cylinder 612.

As best shown in FIGS. 40-42, a suture-retention member 626 can be connected to the distal end of the slotted tube 610. The suture-retention member 626 can have features similar to as described above for suture-retention member 510, including a proximal disc member 638 connected to the distal end of the slotted tube 610, a distal disc member 636, and at least one release member or release wire 628 extending through the proximal and distal disc members for interacting with one or more suture loops 522.

Figure 43:
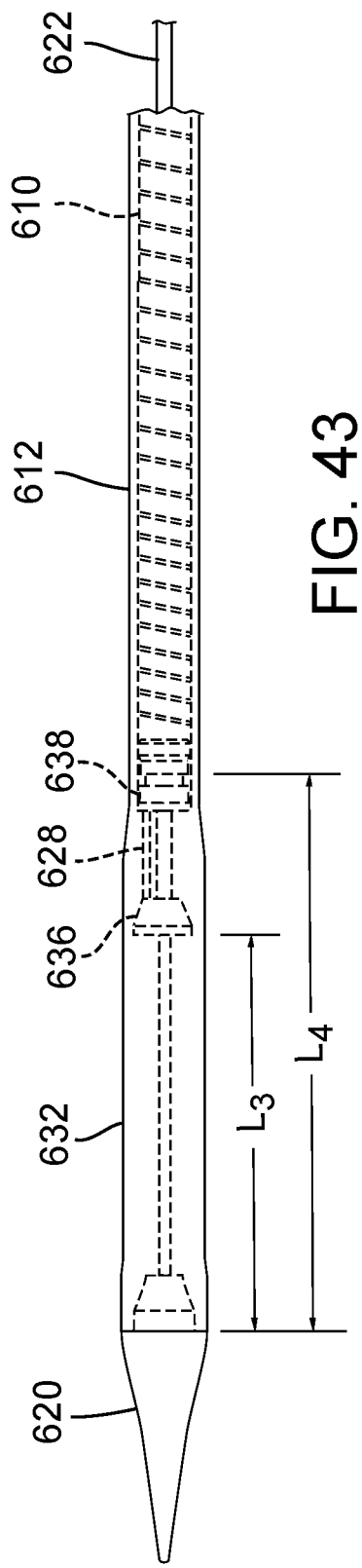
FIG. 43 is a detailed view of the distal end portion of the delivery apparatus of FIG. 38, with the delivery sheath advanced to its distal-most position for delivery of a prosthetic valve.
Figure 46:
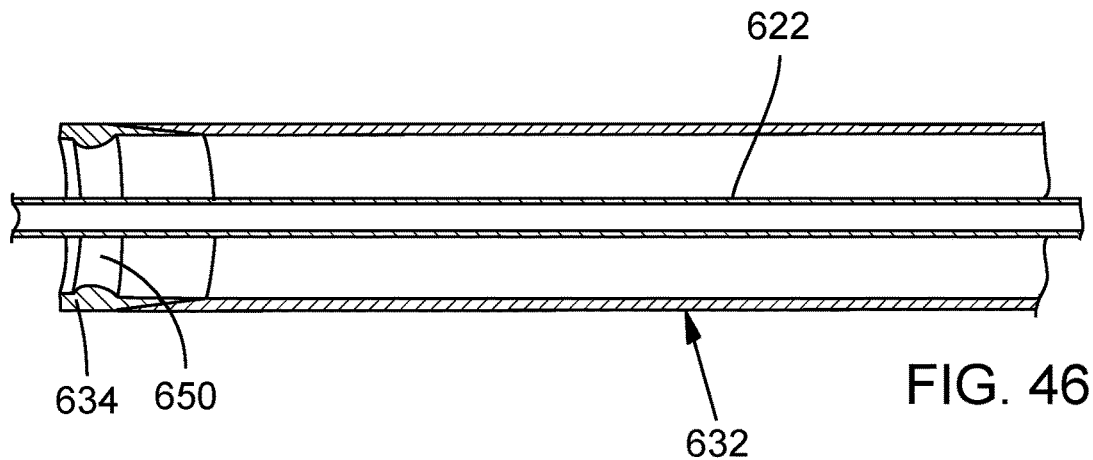
FIG. 46 is an enlarged, cross-sectional view of the distal end portion of a delivery sheath, according to one embodiment.

Returning to FIGS. 39A-39C, the delivery cylinder 612 in the illustrated embodiment comprises a relatively more flexible proximal portion 630 and a relatively less flexible distal end portion 632. The proximal portion 630 can comprise a slotted metal tube or cylinder to enhance the flexibility of this section of the delivery cylinder 612. The distal end portion 632 comprises a sleeve or sheath (also referred to as a "valve holding portion") that is configured to extend over and retain a prosthetic valve in a radially compressed state during delivery. In some embodiments, the sheath 632 can extend over the prosthetic valve and the suture-retention member 626 during delivery (FIG. 43). Alternatively, the suture-retention member 626 can be (at least partially) housed within the proximal portion 630 during delivery. The sheath 632 can be made of a suitable polymeric material, such as PEEK, nylon-12, and/or PEBAX, or a metal having a polymeric inner liner. When made of polymeric materials, the sheath 632 can be thermally bonded to the slotted tube 630. A distal end segment 634 of the sheath 632 can be flared radially outward to enhance recapturability of the prosthetic valve. The distal end segment 634 can comprise a polymeric and/or elastomeric material, such as PEEK, nylon, and/or PEBAX. In particular embodiments, the distal end segment 634 is more flexible and/or elastomeric than the remaining section of the distal end portion. In a working embodiment, the distal end segment 634 comprises PEBAX and the remaining portion of the distal end portion 632 comprises nylon. As shown in FIG. 46, the distal end segment 634 can include a radially projecting, annular bump 650 to facilitate loading and recapturing of a prosthetic valve. During recapture, the bump 650 presses the sutures 522 inwardly, which causes the apices 302, 306 to collapse inwardly, allowing the sheath to slide over the frame.

As shown in FIG. 42, the delivery apparatus 600 can further comprise a nose cone 620 connected to the distal end of a nose cone shaft 622, which extends through the distal shaft portion 610 of the first catheter 602, the suture retention member 626, and the screw 618 and the shaft 614 of the second catheter 604. The nose cone shaft 622 can include a guidewire lumen and can extend proximally to the handle of the delivery apparatus.

The delivery cylinder 612 cooperates with the screw 618 and the nut 640 to allow for longitudinal (i.e., proximal and/or distal) movement of the delivery cylinder 612 relative to the distal shaft portion 610 and the suture-retention member 626. Rotational motion of the screw 618 (initiated by the user rotating the torque shaft 614) can be converted into translational movement of the delivery cylinder 612 via the nut 640 positioned along external threads of the screw 618 (FIG. 39B). The nut 640 can have internal threading configured to compatibly engage the external threads of the screw member 618. The nut 640 can further comprise one or more tabs 642 protruding radially outward, and the delivery cylinder 612 can comprise one or more receiving areas (such as one or more windows 644) adjacent a proximal end of the cylinder 612 for engaging with these tabs 642. In particular, upper portions of the tab(s) 642 can extend through the window(s) 644 to produce a secure fit (e.g., a snap fit) with the delivery cylinder 612.

As noted above, the first catheter 602 includes a section 608 that includes a plurality of angularly spaced rails 613, which cooperate with the tab(s) 642 of the nut. As best shown in FIG. 41, the screw 618 extends coaxially through the rails 613 and the nut 640 is disposed on the screw 618 with each tab 642 positioned in the space between two adjacent rails 613. To produce movement of the delivery cylinder 612, the screw 618 can be rotated using a torque shaft 614, as described above with respect to delivery apparatus 100. Placement of the tab(s) 642 between the rails 613 prevents the nut 640 from rotating along with the screw 618. With rotation of the nut 640 restricted, rotation of the screw 618 produces translational movement of the nut 640 along the screw 618. Axial movement of the nut 640 along the screw 618 (in the distal or proximal direction) causes the cylinder 612 to also move axially, and in the same direction as the nut 640 (relative to the screw 618). Thus, as the nut 640 moves along the screw 618 longitudinally, the delivery cylinder 612 (connected to the nut at windows 644) is carried along-with.

An outer sleeve portion 648 can be positioned over the first and second catheters 602, 604 (FIG. 41) and the delivery cylinder 612, and thereby form an outermost layer of the delivery apparatus 600. This sleeve portion 648 allows a user to effectively flush the delivery apparatus 600 with fluid to, for example, eliminate air bubbles. In some embodiments, the sleeve portion 648 can comprise an elastomeric material and/or may be affixed to the delivery cylinder 612 at one or more locations. In particular, a sleeve portion 648 having elastomeric properties can be affixed to both the delivery cylinder 612 and the elongated shaft 606 of the first catheter 602 (proximal to the intermediate section 608). In this case, the sleeve portion 648 can stretch, between the cylinder 612 and the shaft 606, as the nut 640 and delivery cylinder 612 are advanced, and relax when these components are retracted. In some embodiments, the sleeve portion 648 is substantially rigid and/or is only affixed to the delivery cylinder 612. In such cases, the entire sleeve portion 648 can be advanced distally or retracted proximally along with the delivery cylinder 612 relative to the first catheter.

In the case of a screw 618 and a nut 640 with standard-type threading, clockwise rotation of the screw 618 can result in proximal movement of the nut 640 along the screw 618. Conversely, counter-clockwise rotation of the standard screw 618 can result in distal movement of the nut 640. In this manner, rotation of the screw 618 can cause proximal or distal movement of the delivery cylinder 612 connected to the nut 640. Alternatively, the threads of the screw can be reversed such that counter-clockwise rotation of the screw causes proximal movement of the nut and clockwise movement of the nut causes distal movement of the nut.

FIG. 43 shows the delivery cylinder 612 advanced forward to its distal-most position for delivery. In the delivery configuration, the distal end portion 632 extends over a prosthetic valve (not shown), which is retained in a radially compressed state and releasably connected to the suture retention member 626 with a plurality of sutures 522. The distal end of the delivery cylinder 612 can abut an annular shoulder of the nose cone 620 (as shown in FIG. 43) when the delivery cylinder is in the delivery configuration. FIG. 42 shows the delivery cylinder 612 in a deployment configuration, with the delivery cylinder 612 retracted to a proximal position. In this position, the distal end portion 632 is retracted proximally past the prosthetic valve (allowing the prosthetic valve to expand) and the distal disc member 636 of the suture retention member 626. To release the prosthetic valve from the suture retention member 626, the release wire 628 is retracted such that its distal end is proximal to the second disc member 636, thereby freeing the distal ends 524 of the suture loops 522 from the prosthetic valve.

Replacing the metal-metal connection between the stent and the delivery apparatus with suture loops allows for lower deployment and recapture torques. These reduced torques allow for relocation of the screw mechanism further away from the distal end of the delivery apparatus. Increasing the spacing between the screw 618 and the prosthetic valve advantageously decreases the relatively stiff section of the delivery apparatus occupied by the prosthetic valve at the distal end of the delivery apparatus. Referring to FIG. 43, the portion of the delivery cylinder 612 extending over the prosthetic valve has a length $L_3$ and the overall relatively stiff section of the delivery system 600 (which does not include the length of the nose cone) has a length $L_4$, which in this embodiment corresponds to the length of the delivery cylinder 612 extending over the prosthetic valve and the suture-retention member 626. For example, in some embodiments, $L_4$ is about 1.3× the length of $L_3$. In various other embodiments, the ratio of $L_4$ to $L_3$ is about 1.6 or less, about 1.5 or less, or about 1.4 or less.

Referring to FIGS. 40-41 and 43, the portion of the delivery apparatus 600 extending from the proximal end of the suture retention member 626 to the distal end of the screw 618 (which is equal to the length L2 of the distal shaft portion 610) can be more flexible than the stiff section housing the prosthetic valve (which is equal to the length $L_4$ of the delivery cylinder 612) Desirably, the relatively more flexible section is long enough such that when the delivery system 600 is advanced through the aorta to implant a prosthetic valve at the aortic valve of a subject, the relatively stiff section is positioned in the ascending aorta, the screw 618 is positioned in the descending aorta, and the relatively more flexible portion extending therebetween is positioned in the aortic arch. This greatly facilitates steering of the delivery apparatus through the aortic arch and proper positioning of the prosthetic valve at the aortic annulus.

In various embodiments, for example, a distal end of the screw 618 can be located at least about 5 cm, at least about 10 cm, at least about 15 cm, at least about 20 cm, or at least about 30 cm away from the distal end of the suture-retention member 626 (and a prosthetic valve releasably connected to the suture-retention member 626). In various embodiments, the delivery cylinder 612 can have an overall length $L_1$ between about 3 cm and about 40 cm, between about 5 cm and about 40 cm, between about 10 cm and about 35 cm, between about 15 cm and about 30 cm, or between about 18 cm and about 25 cm. In various embodiments, the distal shaft portion 610 can have an overall length L2 between about 0 cm and about 30 cm, between about 5 cm and about 25 cm, between about 10 cm and about 22 cm, or between about 15 cm and about 20 cm.

In alternative embodiments, the length $L_1$ of the deliver cylinder 612 can be longer than 40 cm, and in some embodiments, it can extend proximally to the handle of the delivery apparatus.

Figure 47:
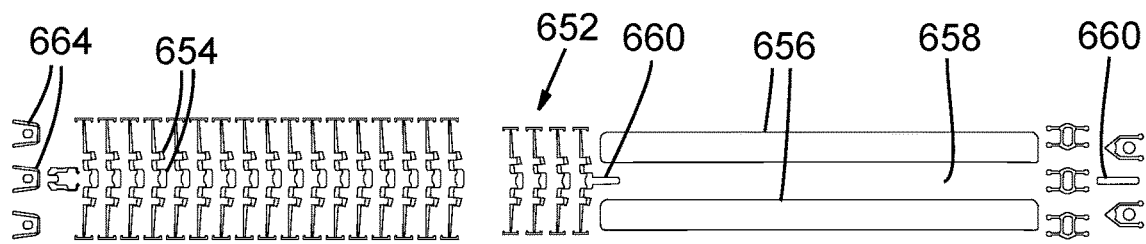
FIG. 47 is a side view of an alternative slotted metal tube that can be used in the delivery apparatus of FIG. 38
Figure 49:
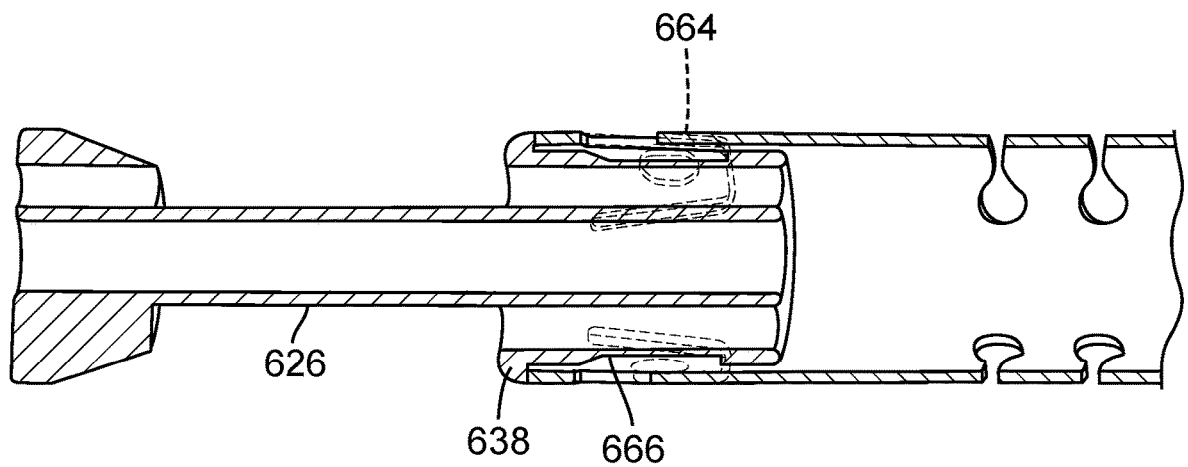
FIG. 49 is an enlarged view of the distal end portion of the slotted metal tube of FIG. 47, shown connected to a suture-retention member.
Figure 48:
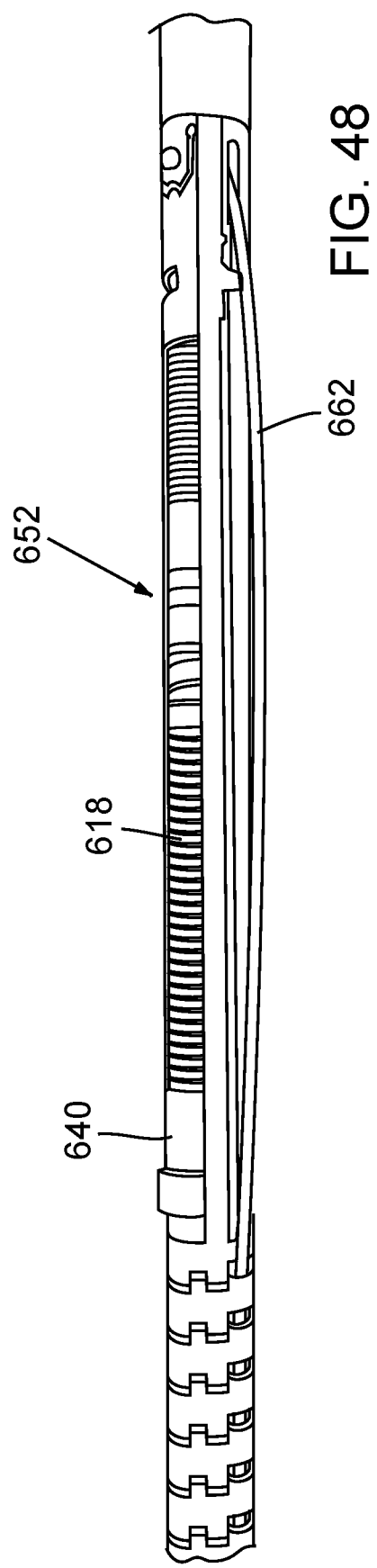
FIG. 48 is a side view of a portion of a delivery apparatus incorporating the slotted metal tube shown in FIG. 47.

FIG. 47 shows an alternative slotted tube 652 that can be used in place of slotted tube 610 in the delivery apparatus 600. The slotted tube 652 has a plurality of teeth or projections 654 formed in each turn or coil that extend into respective recesses in adjacent coils to increase torque resistance. A distal end of the tube can be formed with one or more longitudinal openings 656, forming rails 658 between adjacent openings for cooperating with the projections 642 of the nut 640. At the distal and proximal ends of the rails 658, the tube can be formed with openings 660 to allow a pull wire 662 to extend through the openings and alongside the screw 618 on the outside of the slotted tube 652. A proximal end of the tube 652 can be formed with a plurality of inwardly projecting tabs 664. As shown in FIG. 49, the tabs 664 can engage an annular recessed portion 666 on the outer surface of the proximal member 638 of the suture-retention member 626. The tabs 664 can be configured to form a snap-fit connection with the proximal member 638 sufficient to secure the suture-retention member to the slotted tube.

In alternative embodiments, the slotted tube 610 and the slotted tube 630 can have other patterns or configurations, such as any of those shown in FIG. 12, 28A, 28B, 29A, or 29B.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and sub-combinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention.

In view of the many possible embodiments to which the principles of the disclosed invention may be applied, it should be recognized that the illustrated embodiments are only preferred examples of the invention and should not be taken as limiting the scope of the invention. Moreover, additional embodiments are disclosed in U.S. Patent Application Publication No. 2010/0049313 (U.S. application Ser. No. 12/429,040), which is incorporated herein by reference. Accordingly, the scope of the invention is defined by the following claims. We therefore claim as our invention all that comes within the scope and spirit of these claims.

We claim:

1. A delivery apparatus for implanting a prosthetic valve, comprising:
   a first elongated shaft having a proximal end portion and a distal end portion;
   a second elongated shaft extending through the first shaft and having a proximal end portion and a distal end portion, the second shaft being rotatable relative to the first shaft but fixed against axial movement relative to the first shaft; and
   a delivery sheath having a distal end portion configured to receive and retain a prosthetic valve in a compressed delivery state, and a proximal end portion coupled to the distal end portion of the second elongated shaft;
   wherein the second shaft is configured to be rotatable relative to the first shaft without moving axially relative to the first shaft such that rotation of the second shaft causes the delivery sheath to move axially relative to the first and second shafts; and
   wherein the proximal end portion of the delivery sheath is more flexible than the distal end portion of the delivery sheath, wherein the delivery sheath is at least about 5 cm in length and no greater than about 40 cm in length.

2. The apparatus of claim 1, further comprising a screw connected to a distal end of the second shaft, and a nut mounted on the screw and connected to the delivery sheath such that rotation of the second shaft and the screw causes axial movement of the nut relative to the screw, thereby producing axial movement of the delivery sheath.

3. The apparatus of claim 2, sized such that when the apparatus is advanced through the aorta and the prosthetic valve is positioned at the native aortic valve of a patient, the distal end portion of the delivery sheath is positioned in the ascending aorta, the screw is positioned in the descending aorta, and the proximal end portion of the delivery sheath extends through the aortic arch from the distal end portion of the delivery sheath to the nut.

4. The apparatus of claim 1, wherein the proximal end portion of the delivery sheath is between about 2 cm and about 35 cm in length.

5. The apparatus of claim 1, wherein the distal end portion of the first shaft extends through the delivery sheath and comprises a slotted metal tube.

6. The apparatus of claim 1, further comprising:
   a suture-retention member connected to the distal end portion of the first shaft;
   a plurality of suture loops extending from the suture-retention member and configured to extend through openings in a frame of the prosthetic valve; and
   at least one slidable release member configured to extend through the suture-retention member and the suture loops to releasably secure the prosthetic valve to the suture-retention member.

7. The apparatus of claim 6, wherein:
   the suture-retention member comprises a proximal portion and a distal portion spaced axially apart from the first portion;
   the release member is slidable relative to the suture-retention member between a first position extending through the proximal and distal portions of the suture-retention member and a second position in which the release member is retracted to a location proximal of the distal portion of the suture-retention member;
   wherein when the release member is in the first position and the suture loops extend through the openings of the frame and around the release member at a location between the proximal and distal portions, the prosthetic valve is secured to the suture-retention member;
   wherein when the release member is in the second position, the suture loops can slide off a distal end of the release member to release the prosthetic valve from the suture-retention member.

8. The apparatus of claim 6, wherein the at least one release member comprises a plurality of release members extending through the suture-retention member.

9. The apparatus of claim 6, wherein the suture loops are formed from a single length of suture material.

10. The apparatus of claim 6, wherein at least one of the suture loops has a greater thickness than others of the suture loops.

11. The apparatus of claim 1, wherein the proximal end portion of the delivery sheath comprises a slotted metal tube.

12. The apparatus of claim 11, wherein the distal end portion of the delivery sheath comprises a delivery capsule connected to a distal end of the slotted metal tube, the delivery capsule configured to extend over and retain the prosthetic valve in the compressed delivery state.

13. The apparatus of claim 12, wherein the delivery capsule comprises a polymer sleeve.

14. A medical assembly, comprising:
a delivery apparatus and a prosthetic valve;
wherein the delivery apparatus comprises:
- a first elongated shaft having a proximal end portion and a distal end portion;
- a second elongated shaft extending through the first shaft and having a proximal end portion and a distal end portion, the second shaft being rotatable relative to the first shaft but fixed against axial movement relative to the first shaft; and
- a delivery sheath having a distal end portion configured to receive and retain a prosthetic valve in a compressed delivery state, and a proximal end portion coupled to the distal end portion of the second elongated shaft;
- wherein the second shaft is configured to be rotatable relative to the first shaft such that rotation of the second shaft causes the delivery sheath to move axially relative to the first and second shafts;
- wherein the prosthetic valve is located distal to the first shaft and comprises a self-expandable stent having a plurality of apices spaced circumferentially around a first end portion of the stent, wherein each apex has an aperture;
- wherein:
  the suture-retention member comprises a proximal portion and a distal portion spaced from the proximal portion, the proximal portion being coupled to the first shaft;
  the at least one slidable release member extends through the proximal portion and the distal portion of the suture-retention member;
  the plurality of suture loops extend from the proximal portion of the suture-retention member, through the apertures in the apices of the stent, and around the release member at a location between the proximal and distal portions of the suture-retention member, wherein at least one of the suture loops extends through the aperture of every apex; and
  the delivery sheath can be advanced over the prosthetic valve to retain the prosthetic valve in the compressed state and retracted relative to the prosthetic valve to permit radial expansion of the prosthetic valve, while the stent remains connected to the suture-retention member via the suture loops;
- wherein after the entirety of the prosthetic valve is deployed from the delivery sheath, the delivery sheath can be advanced distally back over the prosthetic valve to cause the prosthetic valve to radially collapse as it is recaptured by the delivery sheath.

15. The apparatus medical assembly of claim 14, wherein the at least one release member is slidable relative to the suture-retention member, and when the release member is retracted proximally such that a distal end of the release is proximal to the distal portion of the suture-retention member, the suture loops can slide off the distal end of the release member, thereby releasing the prosthetic valve from the suture-retention member.

* * * * *